United States Patent
Groothuis et al.

(10) Patent No.: US 12,419,633 B2
(45) Date of Patent: *Sep. 23, 2025

(54) DEVICES AND METHODS FOR PERCUTANEOUS TRICUSPID VALVE REPAIR

(71) Applicant: EDWARDS LIFESCIENCES CORPORATION, Irvine, CA (US)

(72) Inventors: Adam Groothuis, Swampscott, MA (US); Steven D. Cahalane, Pelham, NH (US); Richard J. Morrill, North Billerica, MA (US); John Alexander, Pinehurst, NC (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 60 days.

This patent is subject to a terminal disclaimer.

(21) Appl. No.: 18/468,724

(22) Filed: Sep. 17, 2023

(65) Prior Publication Data

US 2024/0000448 A1 Jan. 4, 2024

Related U.S. Application Data

(60) Continuation of application No. 17/171,529, filed on Feb. 9, 2021, now Pat. No. 11,793,505, which is a
(Continued)

(51) Int. Cl.
*A61B 17/04* (2006.01)
*A61B 17/00* (2006.01)

(52) U.S. Cl.
CPC ............ *A61B 17/0401* (2013.01); *A61B 2017/00783* (2013.01); *A61B 2017/0406* (2013.01);
(Continued)

(58) Field of Classification Search
CPC .......... A61B 17/221; A61B 2017/2212; A61B 2017/2215; A61B 2017/2217;
(Continued)

(56) References Cited

U.S. PATENT DOCUMENTS 3,604,488 A 9/1971 Wishart et al.
3,656,185 A 4/1972 Carpentier
(Continued)

FOREIGN PATENT DOCUMENTS

CN 113331995 A 9/2021
EP 1034753 A1 9/2000
(Continued)

OTHER PUBLICATIONS

Agarwal et al. International Cardiology Perspective Functional Tricuspid Regurgitation, Circ Cardiovasc Interv 2009;2;2;565-573 (2009).
(Continued)

*Primary Examiner* — Thomas McEvoy
(74) *Attorney, Agent, or Firm* — Anya Adams

(57) ABSTRACT

A first end of a wire is transluminally penetrated through tissue at a first cardiovascular site of a subject. A capture device is transluminally advanced into the subject, and is used to capture the first end of the wire and pull the first end of the wire away from the first cardiovascular site. From the first end of the wire, a first anchor is tracked along the wire, and is then anchored to the tissue at the first cardiovascular site. A second anchor is anchored to tissue at a second cardiovascular site. Subsequently, the first and second cardiovascular sites are drawn together by applying tension between the first and second anchors. Other embodiments are also described.

15 Claims, 20 Drawing Sheets

Related U.S. Application Data continuation of application No. 16/184,615, filed on Nov. 8, 2018, now Pat. No. 10,918,374, which is a continuation of application No. 15/172,972, filed on Jun. 3, 2016, now Pat. No. 10,130,356, which is a division of application No. 14/190,732, filed on Feb. 26, 2014, now Pat. No. 9,724,084.

(60) Provisional application No. 61/769,738, filed on Feb. 26, 2013.

(52) U.S. Cl.
CPC .............. *A61B 2017/0409* (2013.01); *A61B 2017/0419* (2013.01); *A61B 2017/0464* (2013.01)

(58) Field of Classification Search
CPC ........ A61B 17/0401; A61B 2017/0409; A61B 2017/00783; A61B 2017/0406; A61F 2/2463; A61F 2/2442; A61F 2/2466; A61F 2/2445
See application file for complete search history.

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,332,402 A | 7/1994 | Teitelbaum |
| 5,346,498 A | 9/1994 | Greelis et al. |
| 5,364,408 A | 11/1994 | Gordon |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,733,331 A | 3/1998 | Peredo |
| 5,749,371 A | 5/1998 | Zadini et al. |
| 5,752,963 A | 5/1998 | Allard et al. |
| 5,782,844 A | 7/1998 | Yoon et al. |
| 5,810,746 A | 9/1998 | Goldstein et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 5,993,459 A | 11/1999 | Larsen et al. |
| 6,042,554 A | 3/2000 | Rosenman et al. |
| 6,045,497 A | 4/2000 | Schweich, Jr. et al. |
| 6,048,351 A | 4/2000 | Gordon et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |

(56) References Cited

U.S. PATENT DOCUMENTS

| | | |
|---|---|---|
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,326 B2 | 9/2009 | Ikuta |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |

(56) References Cited

U.S. PATENT DOCUMENTS

| | | |
|---|---|---|
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,594 B2 | 2/2015 | Maisano et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,724,084 B2 | 8/2017 | Groothuis et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,130,356 B2 | 11/2018 | Groothuis et al. |
| 10,368,852 B2 | 8/2019 | Gerhardt et al. |
| 2001/0021874 A1 | 9/2001 | Carpentier et al. |
| 2002/0022662 A1 | 2/2002 | Yardley et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0107531 A1 | 8/2002 | Schreck et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0083538 A1 | 5/2003 | Adams et al. |
| 2003/0105519 A1 | 6/2003 | Fasol et al. |

(56) References Cited

U.S. PATENT DOCUMENTS

| | | |
|---|---|---|
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0002735 A1 | 1/2004 | Lizardi et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0059413 A1 | 3/2004 | Argento |
| 2004/0068273 A1 | 4/2004 | Fariss et al. |
| 2004/0106950 A1 | 6/2004 | Grafton et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0162610 A1 | 8/2004 | Liska et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0225233 A1 | 11/2004 | Frankowski et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075654 A1 | 4/2005 | Kelleher |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1 | 10/2005 | Martinek et al. |
| 2005/0251177 A1 | 11/2005 | Saadat et al. |
| 2005/0256532 A1 | 11/2005 | Nayak et al. |
| 2005/0267478 A1 | 12/2005 | Corradi et al. |
| 2005/0267571 A1 | 12/2005 | Spence et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0173251 A1 | 8/2006 | Govari et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0212048 A1 | 9/2006 | Crainich |
| 2006/0229708 A1 | 10/2006 | Powell et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0060922 A1 | 3/2007 | Dreyfuss |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |

(56) References Cited

U.S. PATENT DOCUMENTS

| | | |
|---|---|---|
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0033460 A1 | 2/2008 | Ziniti et al. |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086164 A1 | 4/2008 | Rowe |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0228223 A1 | 9/2008 | Alkhatib |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093670 A1 | 4/2009 | Annest et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0292353 A1 | 11/2009 | Yoganathan et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168645 A1 | 7/2010 | Binner et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0210899 A1 | 8/2010 | Schankereli |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0292785 A1 | 11/2010 | Seguin et al. |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0015476 A1 | 1/2011 | Franco |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0060407 A1 | 3/2011 | Ketai et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144576 A1 | 6/2011 | Rothe et al. |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |

(56) References Cited

U.S. PATENT DOCUMENTS

| | | |
|---|---|---|
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0029627 A1 | 2/2012 | Salahieh et al. |
| 2012/0035712 A1 | 2/2012 | Maisano et al. |
| 2012/0053628 A1 | 3/2012 | Sojka et al. |
| 2012/0053642 A1 | 3/2012 | Lozier et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0143226 A1 | 6/2012 | Belson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0203336 A1 | 8/2012 | Annest |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0310840 A1 | 12/2012 | Colombo et al. |
| 2012/0323313 A1 | 12/2012 | Seguin |
| 2013/0018459 A1 | 1/2013 | Maisano et al. |
| 2013/0030522 A1 | 1/2013 | Rowe et al. |
| 2013/0046373 A1 | 2/2013 | Cartledge et al. |
| 2013/0046380 A1 | 2/2013 | Maisano et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0211513 A1* | 8/2013 | Rourke .............. A61B 17/0401 623/2.37 |
| 2013/0218206 A1 | 8/2013 | Gadlage |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163615 A1 | 6/2014 | Gadlage et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0350662 A1 | 11/2014 | Vaturi |
| 2014/0379006 A1 | 12/2014 | Sutherland et al. |
| 2015/0018940 A1 | 1/2015 | Quill et al. |
| 2015/0025553 A1 | 1/2015 | Del Nido et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112429 A1 | 4/2015 | Khairkhahan et al. |
| 2015/0112432 A1 | 4/2015 | Reich et al. |
| 2015/0119936 A1 | 4/2015 | Gilmore et al. |
| 2015/0119979 A1 | 4/2015 | Maisano et al. |
| 2015/0127097 A1 | 5/2015 | Neumann et al. |
| 2015/0133997 A1 | 5/2015 | Deitch et al. |
| 2015/0164637 A1 | 6/2015 | Khairkhahan et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0029920 A1 | 2/2016 | Kronstrom et al. |
| 2016/0030034 A1 | 2/2016 | Graul et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0256149 A1 | 9/2016 | Sampson et al. |
| 2016/0256274 A1 | 9/2016 | Hayoz |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0346084 A1 | 12/2016 | Taylor et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0100119 A1 | 4/2017 | Baird et al. |
| 2017/0224489 A1 | 8/2017 | Starksen et al. |
| 2017/0245993 A1 | 8/2017 | Gross et al. |
| 2018/0008409 A1 | 1/2018 | Kutzik et al. |
| 2018/0049875 A1 | 2/2018 | Iflah et al. |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0280019 A1 | 10/2018 | Azar et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0091445 A1 | 3/2019 | House |
| 2019/0111239 A1 | 4/2019 | Bolduc et al. |
| 2019/0117113 A1 | 4/2019 | Curran |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0159898 A1 | 5/2019 | Kutzik et al. |

(56) References Cited

U.S. PATENT DOCUMENTS

| | | |
|---|---|---|
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0240023 A1 | 8/2019 | Spence et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015810 A1 | 1/2020 | Piccirillo |
| 2020/0015971 A1 | 1/2020 | Brauon et al. |
| 2020/0178956 A1 | 6/2020 | Mitelberg et al. |
| 2020/0289267 A1 | 9/2020 | Peleg et al. |
| 2020/0337840 A1 | 10/2020 | Reich |
| 2020/0390551 A1 | 12/2020 | McCarthy |
| 2021/0015475 A1 | 1/2021 | Lau |
| 2021/0052387 A1 | 2/2021 | Greenan et al. |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2021/0145584 A1 | 5/2021 | Kasher et al. |
| 2022/0071620 A1 | 3/2022 | Brauon et al. |
| 2022/0096232 A1 | 3/2022 | Skaro et al. |
| 2022/0110656 A1 | 4/2022 | Azar et al. |
| 2022/0142779 A1 | 5/2022 | Sharon |
| 2022/0176076 A1 | 6/2022 | Keidar |
| 2022/0233316 A1 | 7/2022 | Sheps et al. |
| 2022/0257196 A1 | 8/2022 | Massmann |
| 2022/0273436 A1 | 9/2022 | Aviv et al. |
| 2022/0313438 A1 | 10/2022 | Chappel-Ram |
| 2022/0323221 A1 | 10/2022 | Sharon et al. |
| 2023/0016867 A1 | 1/2023 | Tennenbaum |
| 2023/0218291 A1 | 7/2023 | Zarbatany et al. |
| 2023/0320856 A1 | 10/2023 | Zarbatany et al. |
| 2024/0008985 A1 | 1/2024 | Yuan et al. |
| 2024/0099736 A1 | 3/2024 | Elsheikh et al. |

FOREIGN PATENT DOCUMENTS

| | | |
|---|---|---|
| EP | 3531975 A1 | 9/2019 |
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2007098512 A1 | 9/2007 |
| WO | 2010000454 A1 | 1/2010 |
| WO | WO-2012004679 A2 | 1/2012 |
| WO | WO-2012178115 A2 | 12/2012 |
| WO | 2012176195 A3 | 3/2013 |
| WO | 2014064964 A1 | 5/2014 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |
| WO | 2020240282 A2 | 12/2020 |
| WO | 2021014440 A1 | 1/2021 |
| WO | 2021038559 A1 | 3/2021 |
| WO | 2021038560 A1 | 3/2021 |
| WO | 2022064401 A2 | 3/2022 |
| WO | 2022090907 A1 | 5/2022 |
| WO | 2022101817 A2 | 5/2022 |
| WO | 2022153131 A1 | 7/2022 |
| WO | 2022157592 A1 | 7/2022 |
| WO | 2022172108 A1 | 8/2022 |
| WO | 2022172149 A1 | 8/2022 |
| WO | 2022200972 A1 | 9/2022 |
| WO | 2022224071 A1 | 10/2022 |
| WO | 2022229815 A1 | 11/2022 |
| WO | 2022250983 A1 | 12/2022 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al."Novel Suture Device for Beating-Heart Mitral Leaflet Approximation", Ann Thorac Surg. 2002, 74:1488-1493.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

Amplatzer® Cribriform Occluder. A patient guide to Percutaneous, Transcatheter, Atrial Septal Defect Closuer, AGA Medical Corporation, Apr. 2008.

Amplatzer® Septal Occluder. A patient guide to the Non-Surgical Closuer of the Atrial Septal Defect Using the Amplatzer Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success-midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept." Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. RING+STRING, Successful Repair technique for ischemic mitral regurgitation with severe leaflet Tethering, The Department of Thoracic Cardiovascular surgery, Hamburg, Germany, Nov. 2008.

Maisano, "The double-orifice technique as a standardized approach to treat mitral," European Journal of Cardio-thoracic Surgery 17 (2000) 201-205.

O'Reilly S et al., "Heart valve surgery pushes the envelope," Medtech Insight 8(3): 73, 99-108 (2006).

Odell JA et al., "Early Results 04yf a Simplified Method of Mitral Valve Annuloplasty," Circulation 92:150-154 (1995).

Park, Sang C. et al. "A percutaneously adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

Swenson, O. An experimental implantable urinary sphincter. Invest Urol. Sep. 1976;14(2):100-3.

Swenson, O. and Malinin, T.I., 1978. An improved mechanical device for control of urinary incontinence. Investigative urology, 15(5), pp. 389-391.

Swenson, Orvar. "Internal device for control of urinary incontinence." Journal of pediatric surgery 7.5 (1972): 542-545.

Tajik, Abdul, "Two dimensional real-time ultrasonic imaging of the heart and great vessels", Mayo Clin Proc. vol. 53:271-303, 1978.

(56) References Cited

OTHER PUBLICATIONS

Alfieri O., et al., "Novel Suture Device for Beating-Heart Mitral Leaflet Approximation," The Annals of Thoracic Surgery, 2002, vol. 74, pp. 1488-1493.

* cited by examiner

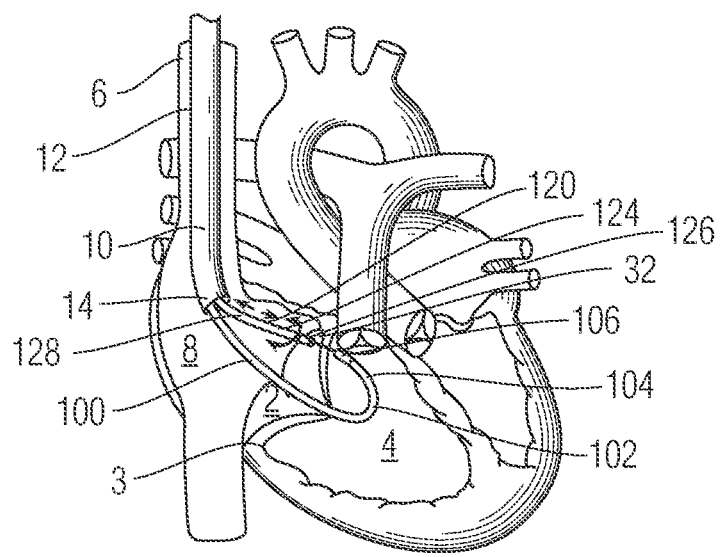
Fig. 7b
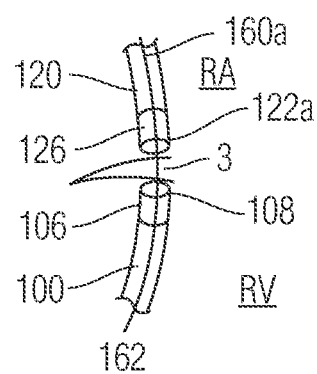
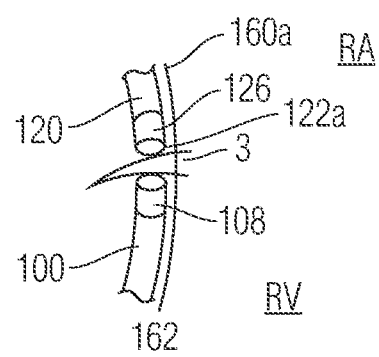
Fig. 7c          Fig. 7d

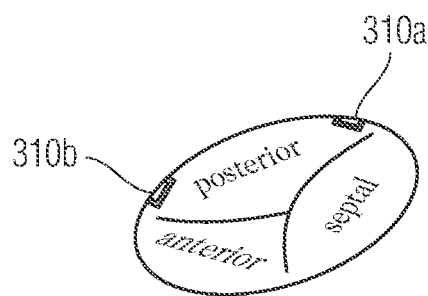
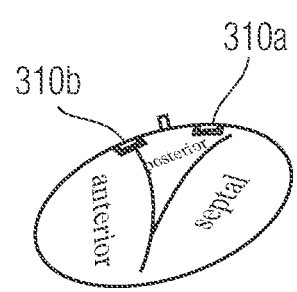
Fig. 16a    Fig. 16b
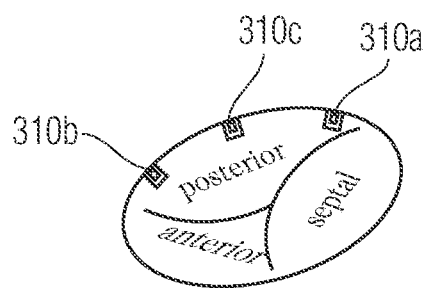
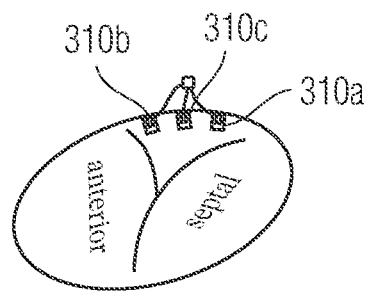
Fig. 16c    Fig. 16d

DEVICES AND METHODS FOR PERCUTANEOUS TRICUSPID VALVE REPAIR

CROSS REFERENCE TO RELATED APPLICATIONS

This application is a Continuation of U.S. patent application Ser. No. 17/171,529 to Groothuis et al., filed Feb. 9, 2021; which is a Continuation of U.S. patent application Ser. No. 16/184,615 to Groothuis et al., filed Nov. 8, 2018 (now U.S. Pat. No. 10,918,374); which is a Continuation of U.S. patent application Ser. No. 15/172,972 to Groothuis et al., filed Jun. 3, 2016 (now U.S. Pat. No. 10,130,356); which is a Divisional of U.S. patent application Ser. No. 14/190,732 to Groothuis et al., filed Feb. 26, 2014 (now U.S. Pat. No. 9,724,084); which claims the benefit of U.S. Provisional Patent Application 61/769,738 to Groothuis et al., filed Feb. 26, 2013, each of which is hereby incorporated by reference in its entirety.

TECHNICAL FIELD

The present teachings generally relate to percutaneous valve repair. Some embodiments of the present teachings relate to percutaneous tricuspid valve repair.

BACKGROUND

Tricuspid valve diseases relate to conditions in which the valve between the two right heart chambers (i.e., the right ventricle and the right atrium) doesn't function properly and they often occur with other heart valve problems. An example of tricuspid valve diseases is tricuspid valve regurgitation, where the tricuspid valve doesn't close properly and blood flows back into the right atrium. Another example is tricuspid valve stenosis where the tricuspid valve is narrowed, which reduces the amount of blood flowing into the right ventricle. Yet another example is tricuspid atresia, a congenital heart disease, where a solid wall of tissues blocks the blood from flowing between the two right heart chambers. Yet another example is the Ebstein's anomaly where a malformed tricuspid valve situates at a position lower than the normal in the right ventricle, causing blood to flow back into the right atrium. There are other tricuspid valve diseases generally known to a person with ordinary skill in the art and these tricuspid valve diseases are also included in the present teachings.

A tricuspid valve disease can be corrected by an annuloplasty ring. In some instances, this device is preferred for surgically repairing a defect tricuspid valve. An annuloplasty ring is an anatomically-correct three-dimensional (3D) ring and can flexibly conform to the heart valve opening. This ring is implanted into a defect tricuspid valve and reduces the valve opening. Properly implanted, an annuloplasty ring allows the valve to open and close properly.

Tricuspid valve repair surgery can be done in one of two ways: a minimally invasive surgery or an open-heart surgery. A minimally invasive method involves making a small upper or lower chest incision and inserting valve repairing system/device percutaneously. After the valve is repaired, the incision is closed with dissolving sutures. Advantages of a minimally invasive approach include a shorter recovery time, less post-operation pain, and earlier return to work and normal daily activities.

SUMMARY

One aspect of the present teachings provides a method for percutaneously reducing the circumference of a tricuspid annulus. This method includes a number of steps, the sequence of which can be changed and each of which can be omitted or modified without the method falling outside the scope of the present teachings. An exemplary step includes positioning a wire delivery catheter through the tricuspid valve into the right ventricle. Another exemplary step includes contacting a distal end of the wire delivery catheter with the tricuspid annulus inside the right ventricle at a first location. Another exemplary step includes advancing one end of a wire from the right ventricle across the tricuspid annulus to the right atrium at the first location, where the wire tracks through an axial lumen of the wire delivery catheter. Another exemplary step includes capturing the end of the wire with a capture device deployed inside the right atrium. Another exemplary step includes retracting the capture device proximally to bring the end of the wire outside of the body. Another exemplary step includes tracking a first tissue anchor delivery catheter over the wire and extending the first tissue anchor delivery catheter across the tricuspid annulus so that a distal end of the first tissue anchor delivery catheter resides inside the right ventricle. Another exemplary step includes deploying a first tissue anchor with a distal portion of the tissue anchor positioning against the tricuspid annulus from inside the right ventricle and a proximal portion of the tissue anchor positioning against the tricuspid annulus from inside the right atrium. Another exemplary step includes retracting the end of the wire back into the axial lumen of the wire delivery catheter.

Another exemplary step includes positioning the wire delivery catheter with the distal end of the wire delivery catheter contacting the tricuspid annulus inside the right ventricle at a second location. Another exemplary step includes advancing the end of the wire from the right ventricle across the tricuspid annulus to the right atrium. Another exemplary step includes capturing the end of the wire with a capture device deployed inside the right atrium. Another exemplary step includes retracting the capture device proximally and thereby extending the end of the wire outside of the body. Another exemplary step includes tracking a second tissue anchor delivery catheter over the wire. Another exemplary step includes extending the second tissue anchor delivery catheter across the tricuspid annulus at the second location so that a distal end of the second tissue anchor delivery catheter resides inside the right ventricle. Another exemplary step includes deploying a second tissue anchor with a distal portion of the tissue anchor positioning against the tricuspid annulus from inside the right ventricle and a proximal portion of the tissue anchor positioning against the tricuspid annulus from inside the right atrium. Another exemplary step includes reducing the distance between the first and second tissue anchors.

In other embodiments, a method for percutaneously reducing the circumference of a tricuspid annulus includes a number of other steps, the sequence of which can be changed and each of which can be omitted or modified without the method falling outside the scope of the present teachings. An exemplary step includes positioning a locating catheter through the tricuspid valve into the right ventricle. Another exemplary step includes contacting a distal end of the locating catheter with the tricuspid annulus inside the right ventricle at a first location. Another exemplary step includes advancing a wire delivery catheter into the right atrium with a distal end of the wire delivery catheter opposing the distal end of the locating catheter and contacting the tricuspid annulus inside the right atrium at the first location. Another exemplary step includes advancing a distal end of a wire from the right atrium across the tricuspid annulus to the right ventricle at the first location, wherein the wire tracks through an axial lumen of the wire delivery catheter. Another exemplary step includes tracking a first tissue anchor delivery catheter over the wire. Another exemplary step includes crossing the tricuspid annulus with a distal end of the first tissue anchor delivery catheter inside the right ventricle. Another exemplary step includes deploying a first tissue anchor with a distal portion of the tissue anchor positioning against the tricuspid annulus from inside the right ventricle and a proximal portion of the tissue anchor positioning against the tricuspid annulus from inside the right atrium. Another exemplary step includes retracting the distal end of the wire back into the axial lumen of the wire delivery catheter. Another exemplary step includes positioning the locating catheter with the distal end of the locating catheter contacting the tricuspid annulus inside the right ventricle at a second location. Another exemplary step includes positioning the wire delivery catheter into the right atrium with the distal end of the wire delivery catheter opposite to the distal end of the locating catheter and contacting the tricuspid annulus inside the right atrium at the second location. Another exemplary step includes advancing the distal end of the wire from the right atrium across the tricuspid annulus to the right ventricle. Another exemplary step includes tracking a second tissue anchor delivery catheter over the wire and crossing the tricuspid annulus at the second location with a distal end of the second tissue anchor delivery catheter inside the right ventricle. Another exemplary step includes deploying a second tissue anchor with a distal portion of the tissue anchor positioning against the tricuspid annulus from inside the right ventricle and a proximal portion of the tissue anchor positioned against the tricuspid annulus from inside the right atrium. Another exemplary step includes reducing the distance between the first and second tissue anchors.

In other embodiments, a method for percutaneously reducing the circumference of a tricuspid annulus includes a number of steps, the sequence of which can be changed and each of which can be omitted or modified without the method falling outside the scope of the present teachings. An exemplary step includes positioning a wire delivery catheter through the tricuspid valve into the right ventricle, wherein a multi-lumen translation catheter is slidably disposed within a lumen of the wire delivery catheter, a first wire is slidably disposed within a first catheter member of the multi-lumen translation catheter, a second wire is slidably disposed within a second catheter member of the multi-lumen translation catheter. Another exemplary step includes positioning a distal end of the first catheter member at a first location. Another exemplary step includes advancing one end of the first wire from the right ventricle across the tricuspid annulus to the right atrium at the first location. Another exemplary step includes expanding the second catheter member of the multi-lumen translation catheter. Another exemplary step includes positioning a distal end of the second catheter member against the tricuspid annulus at a second location. Another exemplary step includes advancing one end of the second wire from the right ventricle across the tricuspid annulus to the right atrium at the second location. Another exemplary step includes capturing the ends of the first and second wires with a capture device. Another exemplary step includes retracting the capture device proximally and extending the ends of the first and second wires outside of the body. Another exemplary step includes tracking a first tissue anchor delivery catheter over the first wire and a second tissue anchor delivery catheter over the second wire. Another exemplary step includes crossing the tricuspid annulus with distal ends of the first and second tissue anchor delivery catheters inside the right ventricle. Another exemplary step includes deploying the first and second tissue anchors with distal portions of the first and second tissue anchors positioning against the tricuspid annulus from inside the right ventricle and proximal portions of the first and second tissue anchors positioning against the tricuspid annulus from inside the right atrium. Another exemplary step includes reducing the distance between the first and second tissue anchors.

In other embodiments, a method for percutaneously reducing the circumference of a tricuspid annulus includes a number of steps, the sequence of which can be changed and each of which can be omitted or modified without the method falling outside of the present teachings. An exemplary step includes positioning a locating catheter through the tricuspid valve into the right ventricle, wherein a multi-lumen translation catheter is slidably disposed within a lumen of the locating catheter and the multi-lumen translation catheter has a first catheter member and a second catheter member. Another exemplary step includes positioning a distal end of the first catheter member at a first location. Another exemplary step includes expanding the second catheter member of the multi-lumen translation catheter and positioning a distal end of the second catheter member against the tricuspid annulus at a second location. Another exemplary step includes advancing first and second wire delivery catheters into the right atrium with distal ends of the first and second wire delivery catheters positioned opposite to the distal ends of the first and second catheter member. Another exemplary step includes contacting the tricuspid annulus inside the right atrium at the first and second locations. Another exemplary step includes advancing distal ends of first and second wires from the right atrium across the tricuspid annulus to the right ventricle at the first and second locations. Another exemplary step includes tracking the first and second tissue anchor delivery catheters over the first and second wires and crossing the tricuspid annulus with distal ends of the first and second tissue anchor delivery catheters inside the right ventricle. Another exemplary step includes deploying the first and second tissue anchors with distal portions of the first and second tissue anchors positioned against the tricuspid annulus from inside the right ventricle and proximal portions of the first and second tissue anchors positioned against the tricuspid annulus from inside the right atrium. Another exemplary step includes reducing the distance between the first and second tissue anchors.

BRIEF DESCRIPTION OF THE DRAWINGS

FIGS. 7a-7b are perspective views of an exemplary locating catheter inserted into the right ventricle in accordance with the present teachings;

FIGS. 7c-7d are perspective views of an exemplary wire across the annulus in accordance with the present teachings;

FIGS. 16a-16f are perspective views of an example of applying tension to multiple exemplary tissue anchors deployed across the tricuspid annulus in accordance with the present teachings;

DETAILED DESCRIPTION OF CERTAIN EMBODIMENTS

Figure 1:
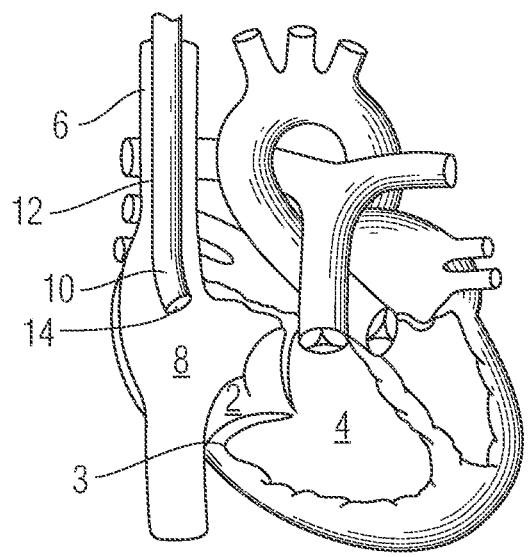
FIG. 1 is a perspective view of an exemplary guide percutaneously inserted into the right atrium in accordance with the present teachings.

Certain specific details are set forth in the following description and figures to provide an understanding of various embodiments of the present teachings. Those of ordinary skill in the relevant art would understand that they can practice other embodiments of the present teachings without one or more of the details described herein. Thus, it is not the intention of the Applicant(s) to restrict or in any way limit the scope of the appended claims to such details.

While various processes are described with reference to steps and sequences in the following disclosure, the steps and sequences of steps should not be taken as required to practice all embodiments of the present teachings.

As used herein, the term "lumen" means a canal, a duct, or a generally tubular space or cavity in the body of a subject, including a catheter, a hollow needle, a tube, a vein, an artery, a blood vessel, a capillary, an intestine, and the like.

As used herein, the term "proximal" shall mean close to the operator (less into the body) and "distal" shall mean away from the operator (further into the body). In positioning a medical device inside a patient, "distal" refers to the direction away from a catheter insertion location and "proximal" refers to the direction close to the insertion location.

As used herein, the term "wire" can be a strand, a cord, a fiber, a yarn, a filament, a cable, a thread, or the like, and these terms may be used interchangeably.

As used herein, the term "sheath" may also be described as a "catheter" and, thus, these terms can be used interchangeably.

The following description refers to FIGS. 1 to 19. A person with ordinary skill in the art would recognize that the figures and description thereto refer to various embodiments of the present teachings and, unless indicated otherwise by their contexts, do not limit the scope of the attached claims to the figures and/or description thereto.

Unless otherwise specified, all numbers expressing quantities, measurements, and other properties or parameters used in the specification and claims are to be understood as being modified in all instances by the term "about." Accordingly, unless otherwise indicated, it should be understood that the numerical parameters set forth in the following specification and attached claims are approximations. At the very least and not as an attempt to limit the application of the doctrine of equivalents to the scope of the attached claims, numerical parameters should be read in light of the number of reported significant digits and the application of ordinary rounding techniques.

The present teachings relate to devices and methods for treating a tricuspid regurgitation. An aspect of the present teachings provides various embodiments of locating a first location on the tricuspid annulus (3) (as shown in FIGS. 1 to 19). According to some embodiments, the first location is on the posterior annulus approximate to the commissure of the posterior and septal leaflets or to the commissure of the posterior and anterior leaflets.

A further aspect of the present teachings provides various embodiments of placing a wire across the tricuspid annulus (3) at the first location. According to some embodiments, the wire crosses the tricuspid annulus (3) from the right atrium to the right ventricle (4) (as shown in FIGS. 1 to 19). According to some embodiments, a wire of the present teachings crosses the tricuspid annulus (3) from the right ventricle to the right atrium (8) (as shown in FIGS. 1 to 19). A further aspect of the present teachings provides various embodiments of deploying a tissue anchor (310a) (as shown, for example, in FIG. 11a) over the wire and across the tricuspid annulus. According to some embodiments, the distal portion of the tissue anchor (310a) is deployed inside the right ventricle (4) and the proximal portion of the tissue anchor (310a) is deployed inside the right atrium (8). According to some embodiments, the distal portion of the tissue anchor (310a) is deployed inside the right atrium (8) and the proximal portion of the tissue anchor (310a) is deployed inside the right ventricle (4).

A further aspect of the present teachings provides various embodiments of locating a second location (30) (as shown, for example, in FIG. 13a) on the tricuspid annulus (3), placing a second wire across the tricuspid annulus (3), and then deploying a second tissue anchor (310b) (as shown, for example, in FIG. 14a) across the tricuspid annulus.

A further aspect of the present teachings provides various embodiments of reducing the circumference of the tricuspid annulus (3). An exemplary method of the present teachings begins by percutaneously accessing the tricuspid annulus (3) from a suitable venous access site. According to some embodiments, the venous access site is located near the jugular vein, superiorly, from the femoral vein, inferiorly, or from other suitable sites. According to some embodiments of the present teachings, as illustrated in FIG. 1, a suitable guide (12) is directed into the internal jugular vein, extends through the right brachiocephalic vein, the superior vena cava (6), and reaches the right atrium (8). The distal end (10) of the guide (12) remains inside the right atrium (8). The proximal end (not shown) of the guide (12) remains outside of the body. According to some embodiments, the guide (12) could have a general straight profile. In another embodiment, the guide (12) could have a curved distal portion. In some embodiments, the distal portion of the guide (12) could have a pre-set fixed curved. In another embodiment, the distal portion of the guide (12) could be deflectable curved section controlled by a clinician from outside of the body. The guide (12) has an axial lumen (14) extending from its proximal end through its entire length to its distal end (10). This axial lumen (14) of the guide (12) serves as a conduit, allowing one or more catheters to be slidably disposed within and providing access to the right heart chambers. According to some embodiments, the guide (12) remains in place as illustrated in FIG. 1 during the entire procedure. According to some embodiments, the guide (12) is removed, for example, during the procedure when other suitable means, such as a wire, maintains such a percutaneous access. According to some embodiments, the guide (12) is a 12 French (F) sheath. According to some embodiments, the guide (12) is a single lumen sheath that can accommodate all subsequent catheters to slide therein. Alternatively, in some embodiments, the guide (12) is a multi-lumen sheath. It will be appreciated by persons of ordinary skill in the art that the size and the exact configuration of the guide (12) is not limited to what is disclosed herein.

In various embodiments, a percutaneous repair of the tricuspid valve (2) starts with identifying and obtaining an access to a first location on the tricuspid annulus (3). FIGS. 2-6 illustrate some embodiments where a wire gains an access to the tricuspid valve (2) from the right ventricle (4) and is advanced across the tricuspid annulus (3) into the right atrium (8). Upon doing so, the distal end of the wire extends from the venous access site through the lumen (14) of the guide (12), reaches the right atrium (8), extends distally through the tricuspid valve (2), reaches the right ventricle (4), advances across the tricuspid valve (2) annulus, and extends proximally out of the body through the lumen (14) of the guide (12). As a result, both ends of the wire are outside of the body.

Figure 2A:
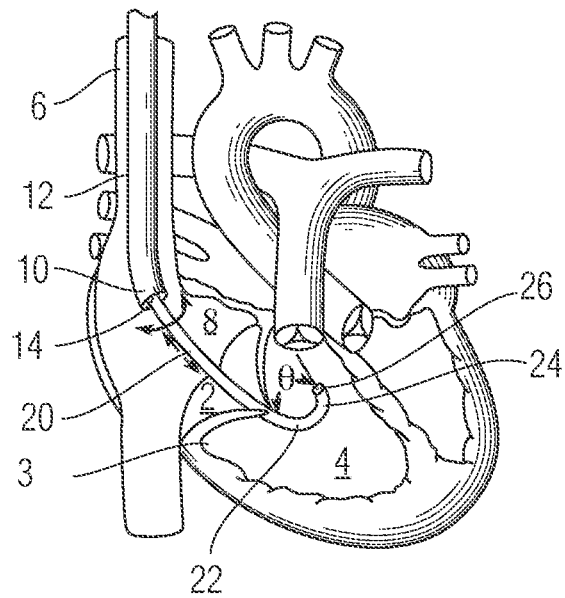
FIGS. 2a-2b are perspective views of an exemplary wire delivery catheter inserted into the right ventricle in accordance with the present teachings.

FIG. 2a illustrates an embodiment where a wire delivery catheter (20) is directed into the right ventricle (4). In one embodiment, a wire delivery catheter is inserted (20) from the proximal end of the guide (12) through the lumen (14) of the guide (12) and reaches the right atrium (8). As shown in FIG. 2a, as the distal end (24) of the wire delivery catheter (20) extends beyond the distal end (10) of the guide (12), the wire delivery catheter (20) is extended further distally through the tricuspid valve (2) and reaches the right ventricle (4). Inside the right ventricle (4), the distal end portion (22) of the wire delivery catheter (20) bends radially away from the longitudinal axis of the wire delivery catheter (20), assuming a curved profile. According to some embodiments, the curved profile of the distal end portion (22) of the wire delivery catheter (20) is in the shape of the letter "J," the letter "U," or any curvature between 90° to 270° as marked as "θ" in FIG. 2a. According to some embodiments, the distal end portion (22) of the wire delivery catheter (20) has a preformed curve, such that as the distal end (24) of the wire delivery catheter leaves the constraint of the guide (12) and enters the right ventricle (4), the distal end portion (22) of the wire delivery catheter (20) resumes its curved profile. According to some other embodiments, the wire delivery catheter (20) has a deflectable distal end portion (22), which is actuated to form a curved profile. One skilled in the art would understand that such an actuation can be accomplished by many mechanisms known in the field. According to some embodiments, the wire delivery catheter (20) can be extended distally, retracted proximally, or turned axially as shown by the double-headed arrows in FIG. 2a.

Figure 2B:
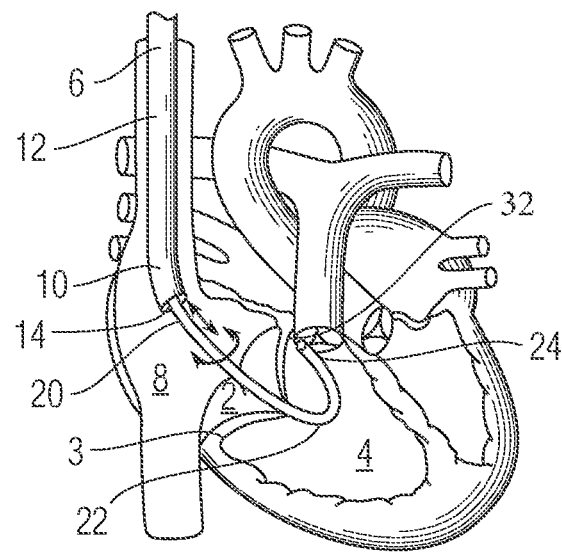

As further illustrated in FIG. 2b, the distal end (24) of the wire delivery catheter (20) is adapted to locate the first location (32) and then make contact with the tricuspid annulus (3) at the right ventricle (4) side.

Anatomically, the right coronary artery is approximately parallel to the circumference of the tricuspid valve (2). The anterior and septal leaflets lie approximately to the proximal half of the right coronary artery. The posterior leaflet of the tricuspid lies approximately to the distal half of the right coronary artery and between the middle of the right coronary artery and the transition of the distal right coronary artery to the posterior descending artery. The middle of the right coronary artery lies approximately next to the commissure of the anterior and posterior leaflets. The transition of the distal right coronary artery to the posterior descending artery, or the proximal posterior descending artery, lies approximately next to the commissure of the septal and posterior leaflets. One skilled in the art would understand that the anatomy of the heart may vary from a subject to another and the present teachings and the attached claims are not limited to the anatomy of any particular subject.

According to some embodiments, a first location (32) is identified by injecting a contrast dye inside the right coronary artery and the distal posterior descending artery. Alternatively, a location can be identified by advancing a radiopaque wire through the right coronary artery to the posterior descending artery. In various embodiments, the contrast dye and/or the radiopaque wire renders the right coronary artery visible under radiographic imaging equipment such as X-ray, magnetic resonance, ultrasound, fluoroscope, or other imaging techniques. By visualizing the right coronary artery and the posterior descending artery, a location can be identified.

Upon identifying the first location (32), in various embodiments, a clinician steers the wire delivery catheter so that, as shown in FIG. 2b, the distal end (24) of the wire delivery catheter (20) aligns at the tricuspid annulus (3), extends toward the right atrium (8), and contacts the tricuspid annulus (3) at the first location (32). According to one embodiment, the first location (32) is at or near the commissure of the septal and posterior leaflets. Alternatively, the first location (32) is at or near the commissure of the anterior and posterior leaflets. One skilled in the art would understand that other locations along the tricuspid annulus (3) can also be used as a first location.

Figure 3A:
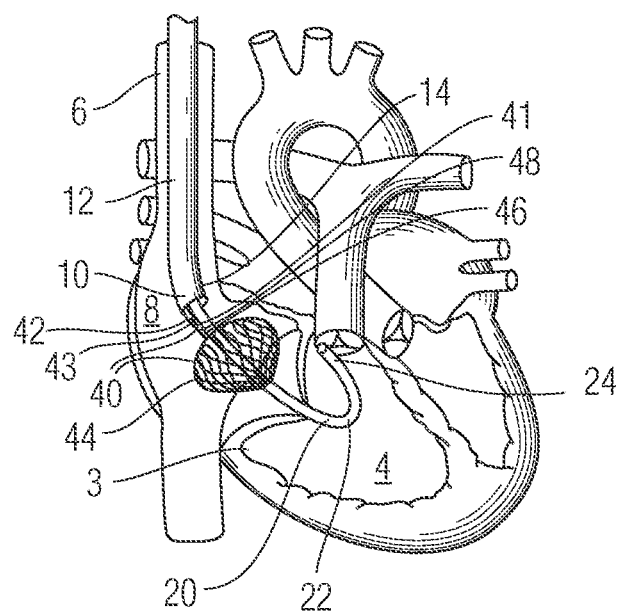
FIGS. 3a-3b are perspective views of an exemplary capture device deployed inside the right atrium in accordance with the present teachings.

In various embodiments, upon aligning the distal end (24) of the wire delivery catheter (20) at the location (32), a capture device (40) is deployed inside the right atrium (8). FIG. 3a illustrates an embodiment where a capture device (40) is advanced distally through the guide (12) and into the right atrium (8). According to some embodiments, a capture device (40) includes a sheath (42) and a capture basket (44). In some embodiments, a capture devices, such as the one illustrated in FIG. 3a, includes a capture basket (44) having an array of shape memory wire mesh on the distal end (48) of a rod (46). According to some embodiments, the capture basket (44) has a radially expanded basket-like profile for capturing the wire as described below and an elongated profile when being constrained within the sheath (42). The capture basket (44) as shown in FIG. 3a is adapted to slide through the axial lumen (41) of the sheath (42), be pushed out of the distal end (43) of the sheath (42), and be retracted back from the distal end (43) of the sheath (42). As the capture basket (44) extends outside of the distal end (43) of the sheath (42), it resumes its expanded profile. As the capture basket (44) is retracted back into the sheath (42), it collapses into its elongated profile. One skilled in the art would understand that the capture basket (44) can be used without the sheath (42), but with the guide (12) alone. Thus what has been described herein should not be viewed as limiting. Additionally, one skilled in the art should understand that although an exemplary embodiment of the capture device has been described in detail herein, other capture device available in the art can also be used for the same purpose to capture the wire. For example a gooseneck snare mechanism can be used. In some embodiment, the snare catheter is constructed of Nitinol cable and with a snare loop. The pre-formed snare loop can be introduced through catheters without risk of snare deformation because of the snare's super-elastic construction. The snare loop is used to capture the distal end of the wire.

In an exemplary use of the device, as illustrated in FIG. 3a, a capture device (40) having a capture basket (44) constrained to its elongated profile within the sheath (42) is directed through the lumen (14) of the guide (12). According to some embodiments, when a multi-lumen sheath is used as the guide, the capture device (40) extends through a separate lumen from the one used by the wire delivery catheter (20). According to other embodiments, when a single-lumen sheath is used as the guide, the capture device (40) extends side-by-side with the wire delivery catheter (20) through the same lumen of the guide. Once the distal end of the capture device (40) is advanced beyond the distal end (10) of the guide (12) and reaches the right atrium (8), the capture basket (44) is further pushed distally outside of the sheath (42) and, being free from the constraint of the sheath (42), the capture basket (44) deploys. The deployed capture basket (44) can at least partially fill the volume of the right atrium (8). One skilled in the art should understand that multiple guides could also be used, one for the delivery capture device, and the other for the delivery of the wire delivery catheter. Thus the exemplary embodiment disclosure herein should be not viewed as limiting.

Figure 3B:
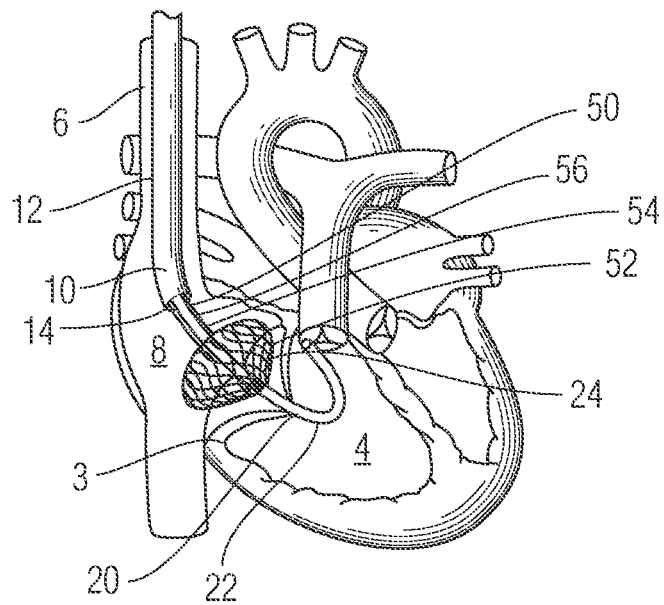

FIG. 3b illustrates another embodiment of the capture device (50). According some embodiments, the capture device (50) includes a capture basket (52) at the distal end (54) of an elongated body (56). The capture device (50), including the elongated body (56) and the capture basket (52) forming an axial lumen, is slidably disposed over the wire delivery catheter (20). Similar to the embodiment shown in FIG. 3a, this capture basket (52) is adapted to slide through the axial lumen (14) of the guide (12). Also similar to the embodiment shown in FIG. 3a, the capture basket (52) has an elongated profile when it is constrained within the lumen (14) of the guide (12) and a radially expanded basket-like profile when it is outside of the guide (12). Similarly, the capture basket (52) can be made of an array of shape memory wire mesh.

According to some embodiments, this capture device (50) is adapted to slide over the wire delivery catheter (20), through the lumen (14) of the guide (12), and be pushed out of the distal end (10) of the guide (12). As the capture device (50) extends outside of the distal end (10) of the guide (12), it resumes its expanded profile. As the capture device (50) is retracted into the lumen (14) of the guide (12), it collapses into its elongated profile. According to some embodiments, the movement of the capture device (50) is independent of the movement of the wire delivery catheter (20). According to other embodiments, the movement of the capture device (50) is dependent to the movement of the wire delivery catheter (20) such that. In certain embodiments, as the distal end (24) of the wire delivery catheter (20) contacts the annulus (3), the capture basket (52) is extended outside of the guide (12) and fully deployed inside the right atrium (8). Although certain embodiments of the capture basket (52) are shown in FIGS. 3a and 3b, one skilled in the art would understand that other capture devices can also be used without departing from the spirit of the present teachings. Thus, what is disclosed in present teachings should not be viewed as limiting.

Besides having a capture basket, according to another embodiment, a capture device includes a sheath with an expandable distal portion or a snare. One skilled in the art would understand that other types of suitable capture devices can also be used here. Thus what is disclosed herein and in FIGS. 3a-3b should not be considered as limiting.

Figure 4A:
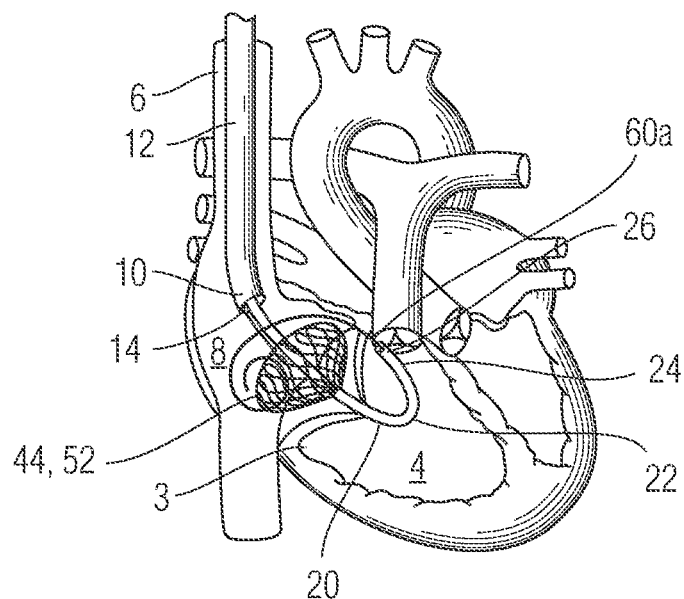
FIGS. 4a-4b are perspective views of an exemplary wire positioned across the annulus in accordance with the present teachings.

In various embodiments, with the capture basket deployed inside the right atrium (8) and the wire delivery catheter (20) properly positioned, a clinician can extend a wire (60a) across the tricuspid annulus (3). Referring to FIG. 4a, a wire is introduced through the wire delivery catheter (20). In the embodiment as illustrated in FIG. 4a, the wire (60a) tracks through the axial lumen (26) of the delivery catheter (20), extends distally from its proximal end, contacts the tricuspid annulus (3), further extends distally, crosses the annulus (3) from the right ventricle (4) side, enters into the right atrium (8), and enters the space filled by the capture basket (44, 52). In some embodiments, the wire is captured by the capture basket.

According to some embodiments, as illustrated in FIG. 4a, the wire (60a) has a piercing tip which allows it to perforate the annulus (3). According to other embodiments, the wire (60a) has a radio frequency (RF) energy delivery tip to assist its crossing of the tricuspid annulus (3). In these other embodiments, a suitable RF energy device (not shown) is coupled to the wire.

Figure 4B:
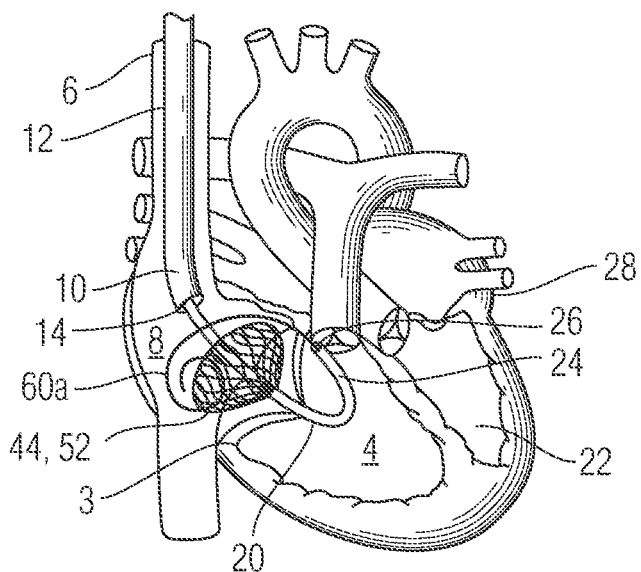

Yet according to other embodiments, as illustrated in FIG. 4b, the wire delivery catheter (20) also includes an extendable needle (28) that is capable of piercing the tricuspid annulus (3). The wire (60a) tracks through the lumen (26) of the such wire delivery catheter (20), extends through the aperture created by the extendable needle (28) of the catheter (20), reaches into the right atrium (8), and enters into the space filled by the capture basket (44, 52). In some embodiments, the wire is captured by the capture basket (44, 52). One skilled in the art would understand that other methods and devices can also be used to access the right atrium (8). Thus, the particular examples described herein should be not viewed as limiting to the scope of the present teachings.

According to some embodiments, the distal portion of the wire (60a) is designed to deflect or curl back to prevent inadvertent tissue damage. The ability to deflect or curl can be achieved by the geometrical construct of the wire (60a), such as a flexible distal portion (62), by the physical property of the material used in making the wire (60a), or by the shape memory property of the material used in making the wire (60a). Those skilled in the art would be able to incorporate known techniques and/or material to achieve this purpose without undue experimentation.

Figure 5:
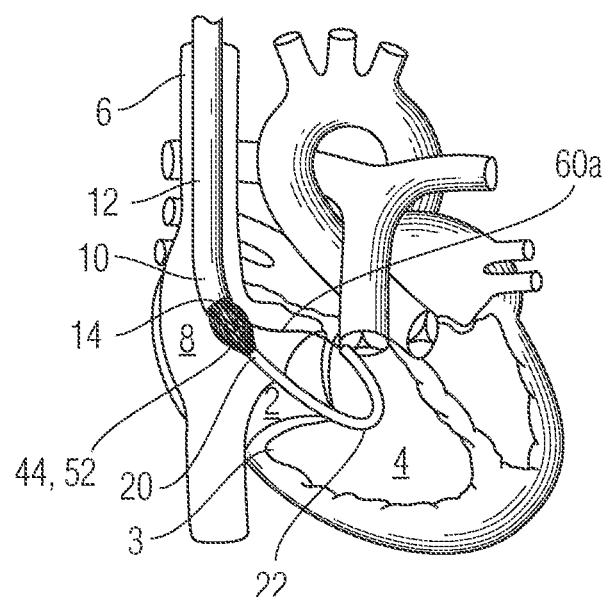
FIG. 5 is a perspective view of an exemplary wire captured and pulled through the guide in accordance with the present teachings.

Now referring to FIG. 5, as the wire enters the right atrium (8) and the space filled by the deployed capture basket (44, 52), it is captured by the capture basket (44, 52) of the capture device (40, 50). As a clinician retracts the capture basket (44) proximally into the sheath (42) or into the guide (12), the capture basket (44, 52) collapses onto the wire (60a). As the clinician further retracts the capture device (40, 50) proximally, the capture device (40, 50) pulls the wire (60a) proximally through the lumen (14) of the guide (12) and out of the body.

Figure 6:
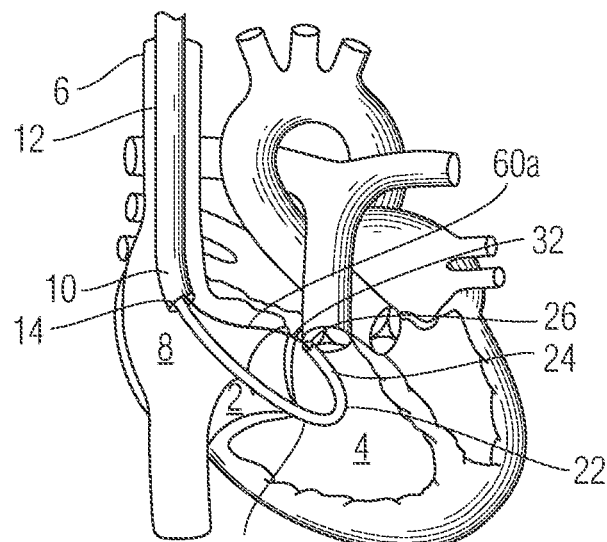
FIG. 6 is a perspective view of an exemplary wire positioned across the annulus in accordance with the present teachings.

In various embodiments, a clinician further retracts the capture device (40), including the sheath (42) and the capture basket (55) as shown in FIG. 3a or including the elongated body (56) with the capture basket (52) as shown in FIG. 3b, proximally through the lumen (14) of the guide (12) outside of the body. By doing this, in some embodiments, the clinician pulls the wire (60a) to the outside of the body. As a result, as shown in FIG. 6, with one end of the wire (60a) remaining outside of the body, the other end extends from the venous access site distally through the lumen (26) of the wire delivery catheter (20), passes the right atrium (8), the tricuspid valve (2), and the right ventricle (4), crosses the tricuspid annulus (3) at a first location (32), extends proximally through the lumen (14) of the guide (12), and exits the venous access site. Thus, with both the ends outside of the body, the wire (60a) maintains an access across the tricuspid annulus (3) at the first location (32) and facilitates the deployment of a tissue anchor (310a) as detailed below.

Figure 8A:
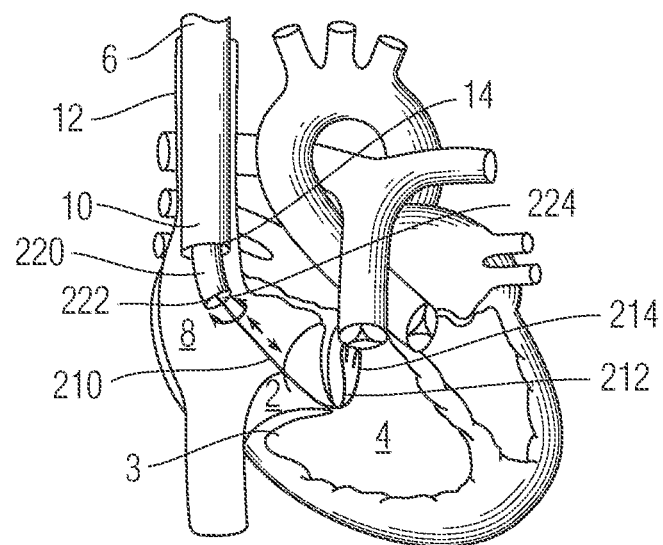
FIGS. 8a-8b are perspective views of an exemplary locating device inserted into the right ventricle in accordance with the present teachings.
Figure 8B:
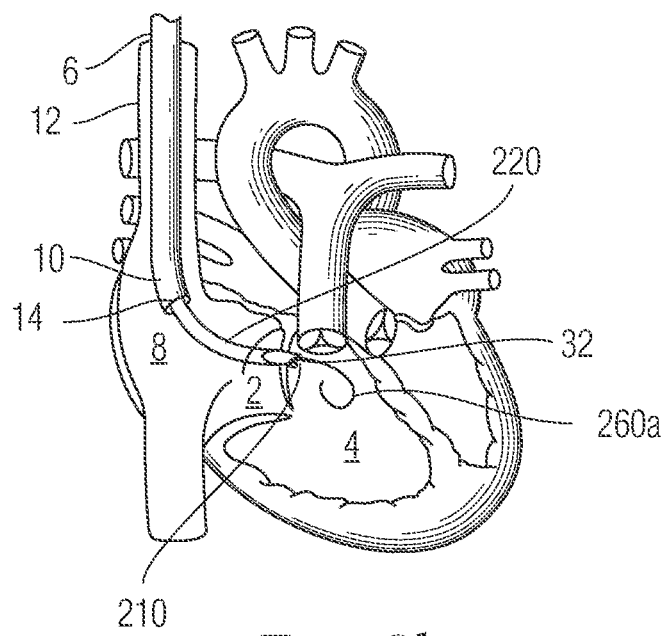
Figure 9:
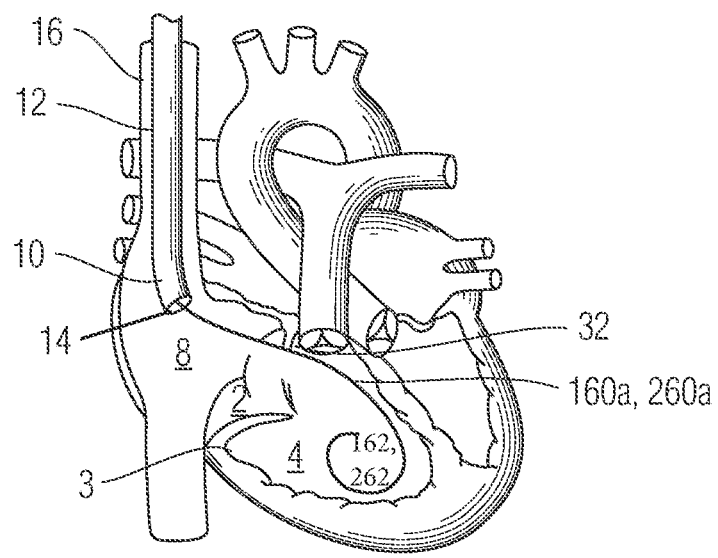
FIG. 9 is a perspective view of an exemplary wire positioned across the annulus in accordance with the present teachings.

FIGS. 7-9 illustrate some embodiments where the wire (160a) extends from the right atrium (8) across the tricuspid annulus (3) into the right ventricle (4) with the proximal end of the wire (160a) outside of the body and the distal end (162) of the wire (160a) inside the right ventricle.

Figure 7A:
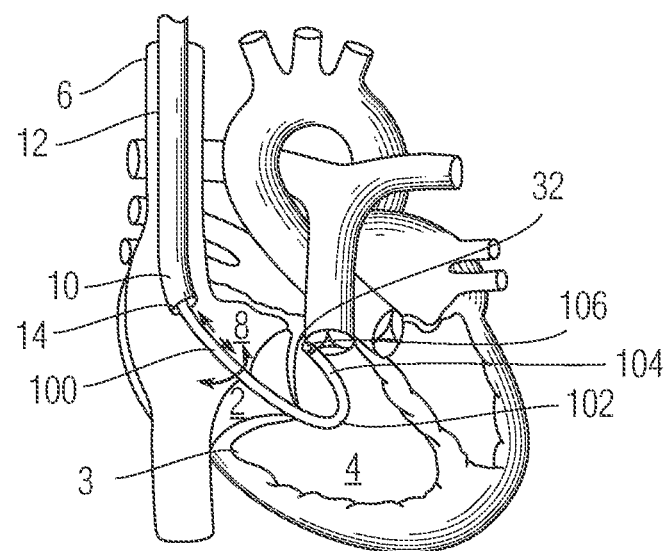

FIGS. 7a-7c illustrate various embodiments where the wire delivery catheter (120) is steered by a locating catheter (100) and positioned against the tricuspid annulus (3) inside the right atrium (8). According to some embodiments, the locating catheter (100) extends distally through the lumen (14) of the guide (12) into the right ventricle (4). In certain embodiments, the locating catheter (100) enters into the right ventricle in a similar manner as the wire delivery catheter (20) described in accordance with FIGS. 2a and 2b. Following the same identification and placement processes as described herein, in various embodiments, the locating catheter (100) is positioned against the tricuspid annulus (3) at the first location (32) inside the right ventricle (4). According to some embodiments, the construct of the locating catheter (100) is similar to the wire delivery catheter (20) described above. In certain embodiments, the locating catheter has a preformed curved distal end portion (102). In certain embodiments, the locating catheter is capable of extending distally and retracting proximally as indicated by the straight double-headed arrows in the FIG. 7a. In certain embodiments, the locating catheter is adapted to turn axially as indicated by the curved double-headed arrows in the FIG. 7a.

Continuing referring to FIG. 7a, in various embodiments, the locating catheter (100) has a magnet (106) at its distal end (104). A wire delivery catheter (120) is advanced distally through the lumen (14) of the guide (12), reaching inside the right atrium (8) and approaching the tricuspid annulus (3). According to some embodiments, the distal end (124) of the wire delivery catheter (120) includes a magnet (126). The magnets (106, 126) on both the locating catheter (100) and the wire delivery catheter (120) have the opposite polarities. Thus, as the wire delivery catheter (120) approaching the tricuspid annulus (3), the magnet in the distal end of the delivery catheter is attracted by the magnet (106) on the distal end (104) of the locating catheter (100). Once the magnets (106, 126) lock up, the tricuspid annulus (3) is sandwiched between the distal ends (124, 102) of the two catheters as illustrated in FIG. 7b.

In various embodiments, a wire (160a) is then advanced from the right atrium (8) across the tricuspid annulus (3) into the right ventricle (4). According to some embodiments, as illustrated in FIG. 7c, the wire (160a) tracks along the axial lumen (122a) of the wire delivery catheter (120) and, upon crossing the tricuspid annulus (3), enters the axial lumen (108) of the locating catheter (100). As the locating catheter (100) retracts proximally, the distal end (162) of the wire (160a) remains inside the right ventricle (4). According to other embodiments, as illustrated in FIG. 7d, the wire (160a) tracks along a side or off-centered axial lumen (122b) of the wire delivery catheter (120) and, upon crossing the tricuspid annulus (3), the distal end (162) of the wire (160a) enters the right ventricle (4). According to some embodiments, the wire delivery catheter (120) also has a deflectable distal end portion (128), which allows this distal end portion (128) deflect radially when the magnet (126) at the distal end (124) of the wire delivery catheter (120) is drawn to the location (32) by the magnet (106) at the distal end (104) of the locating catheter (100), as shown in FIG. 7b. Similarly, the wire delivery catheter (120) can be extended distally and retracted proximally or turned axially, as indicated by the double-headed arrows. According to some embodiments, the design or configuration of the wire (160a) is similar to what is described herein in according with FIGS. 4a and 4b.

FIGS. 8a and 8b illustrate yet other embodiments of the present teachings where a wire delivery catheter (220) is guided by a locating device (210). According to some embodiments, the wire delivery catheter (220) has two axial lumens (222, 224), one for a wire (260a) and the other for a locating device (210). The wire delivery catheter (220) enters the right atrium (8) through the lumen (14) of the guide (12). While maintaining the position of the wire delivery catheter (220) inside the right atrium (8), a clinician can extend the locating device (210) distally through the tricuspid valve (2) into the right ventricle (4) in a similar manner with respect to the wire delivery catheter (20) as described herein in accordance with FIGS. 2a and 2b. Similarly, the locating device (210) can have a curved distal portion (212), either preformed or actuated by a clinician, can be extended distally and retracted proximally, or be turned axially as indicated by the double-headed arrows in the FIG. 8a.

Upon entering the right ventricle (4), the distal end (214) of the locating device (210) is positioned at the first location (32) following the methods described herein in accordance with FIGS. 2a-2b, as well as FIG. 7a. Maintaining the position of the locating device (210) steady, the wire delivery catheter (220) is pushed distally toward the tricuspid annulus (3) so that the annulus (3) is sandwiched between the catheter (220) and the locating device (210), as shown in FIG. 8b. A wire (260a) is advanced distally from the wire lumen (224) across the tricuspid annulus (3) and into the right ventricle (4), as shown in FIG. 8b. According to some embodiments, the distal end (214) of the locating device (210) has openings or slots. In some embodiments, when the wire (260a) advances across the tricuspid annulus (3), it enters the openings or slots in the distal end (214) of the locating device (210). In other embodiments, the distal end (214) of the locating device (210) is configured that when a clinician retracts the locating device (210) proximally, he/she would not disturb the wire (260a). According to some embodiments, the design and configuration of the wire (260a) is similar to what is described herein according to FIGS. 4a and 4b. One skilled in the art would understand that the particular embodiments in FIGS. 8a and 8b only illustrate certain aspects of the present teachings and that they should not be viewed as limiting the scope of the present teachings.

According to some embodiments, upon placing the wire (160, 260) across the first location (32) on the tricuspid annulus (3), the wire delivery catheter (120, 220), the locating catheter (100), and/or the locating device (210) are retracted proximally outside of the body. FIG. 9 illustrates that the wire (160, 260) extends distally from a venous access site, tracks along the lumen of the wire delivery catheter (120, 220), enters into the right atrium (8), crosses the tricuspid annulus (3), and reaches the right ventricle (4). The proximal end of the wire (160, 260) remains outside of the body and is controlled by a clinician. The distal end (162, 262) of the wire (160, 260) remains inside the right ventricle (4). In some embodiments, the wire (160, 260) has a piercing tip which allows it to perforate the tricuspid annulus (3) or has a radio frequency energy delivery tip which delivers a radio frequency energy to the annulus tissue to perforate the tricuspid annulus (3). Additionally, similar to what is described herein according to FIGS. 4a and 4b, the distal portion of the wire is designed to deflect or curl back to prevent inadvertent tissue damage, as shown in FIG. 9.

Figure 10:
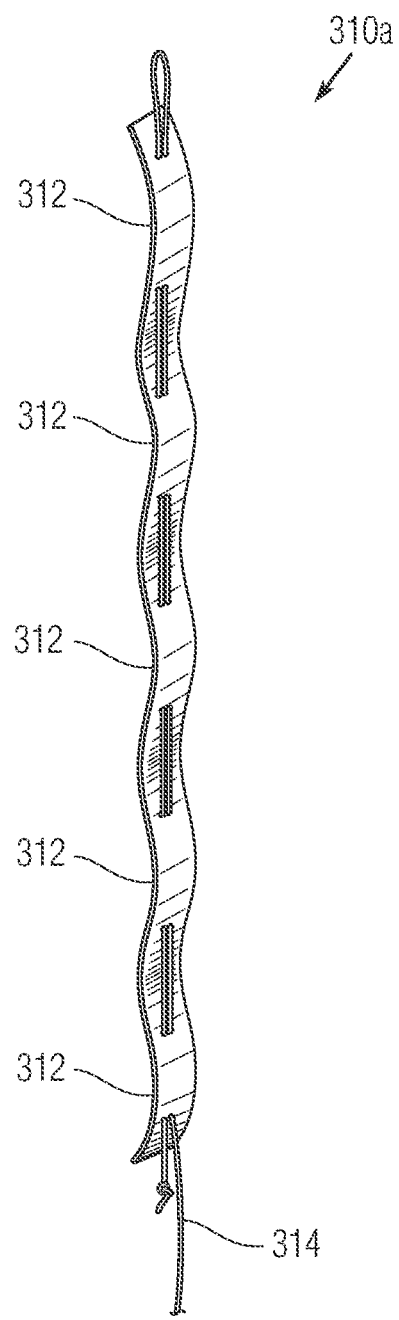
FIG. 10 is a perspective view of an exemplary tissue anchor in accordance with the present teachings.

With the wire (60a, 160a, 260a) in place across the tricuspid annulus (3), in various embodiments, a tissue anchor (310a) is deployed at a location. According to some embodiments, as illustrated in FIGS. 10-12, a first tissue anchor delivery catheter (300) is tracked along the wire (60a, 160a, 260a), across the tricuspid annulus (3), and into the right ventricle (4). In certain embodiments, the tissue anchor delivery catheter (300) is used to deliver a tissue anchor (310a) to the tricuspid annulus (3).

While any tissue anchoring devices known in the art can be used, the particular tissue anchor (310a) in the present teachings, as shown in FIG. 10, is collapsible. In various embodiments, a tissue anchor comprises a plurality of discrete, flat, or flexible anchor elements (312) coupled with a flexible tensile member (314). The anchor elements (312) can be made from a surgical grade fabric material (e.g., a polyester material such as DACRON), in some instances, designed to promote tissue in-growth so that the anchors (310a) become at least in part encased in tissue over-time. The anchor elements (312) are coupled to a tensile member (314), in this example, a suture, by threading the suture distally through the anchor elements (312) and proximally through the anchor elements (312). A slip knot or another type of locking mechanism is formed so that when a proximal end portion of the tensile member (314) is pulled, all of the anchor elements (312) will be drawn together. This leaves a long "tail" of the suture leading from the anchor to the venous access site and the long "tail" can be used for subsequent tensioning and plication, as described herein.

Examples of a tissue anchor (310) and a tissue anchor delivery catheter (300) described in conjunction with the drawings of the present teachings have some similarities to those in U.S. patent application Ser. No. 12/273,670, filed on Nov. 19, 2008, entitled Tissue Anchor and Anchoring System, U.S. patent application Ser. No. 11/174,951, filed on Jul. 5, 2005, entitled Tissue Anchor, Anchoring System and Methods of Using the Same, U.S. patent application Ser. No. 13/777,042, filed on Feb. 26, 2013, entitled Tissue Anchor and Anchoring System, each of which is incorporated by reference herein in its entirety. Though not shown in the exemplary figures, other suitable tissue anchors can also be used. Examples of suitable tissue anchors include, but are not limited to, tissue fasteners, tissue pledgets, or tissue staples etc.

Figure 11A:
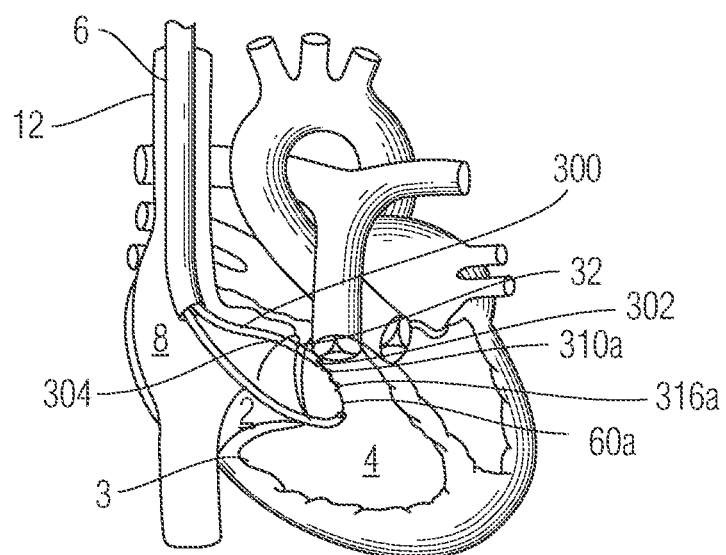
FIGS. 11a-11c are perspective views of an exemplary tissue anchor deployed across the tricuspid annulus in accordance with the present teachings.
Figure 11B:
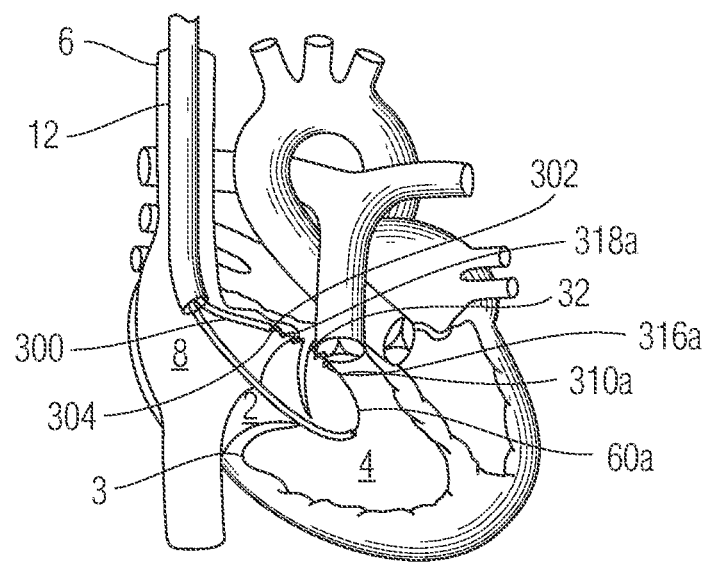
Figure 11C:
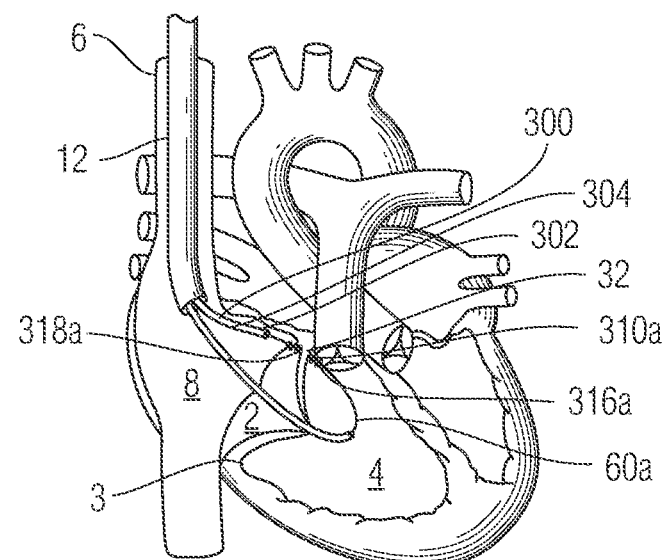
Figure 12A:
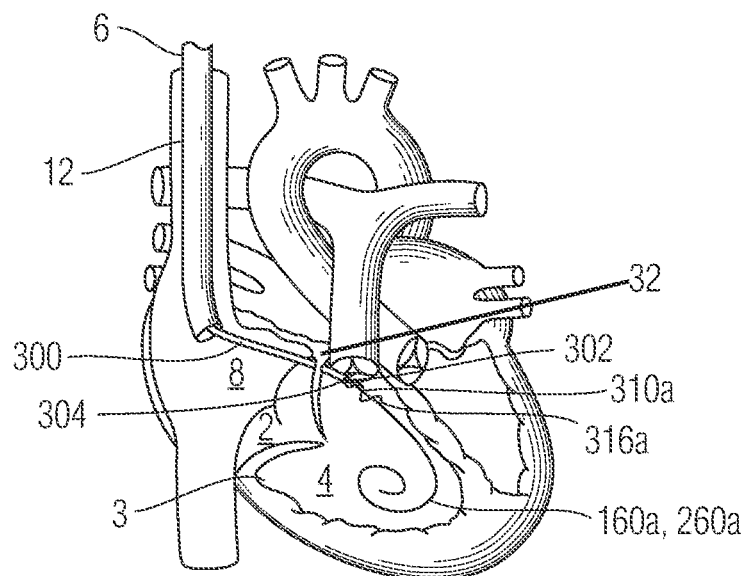
FIGS. 12a-12c are perspective views of an exemplary tissue anchor deployed across the tricuspid annulus in accordance with the present teachings.
Figure 12B:
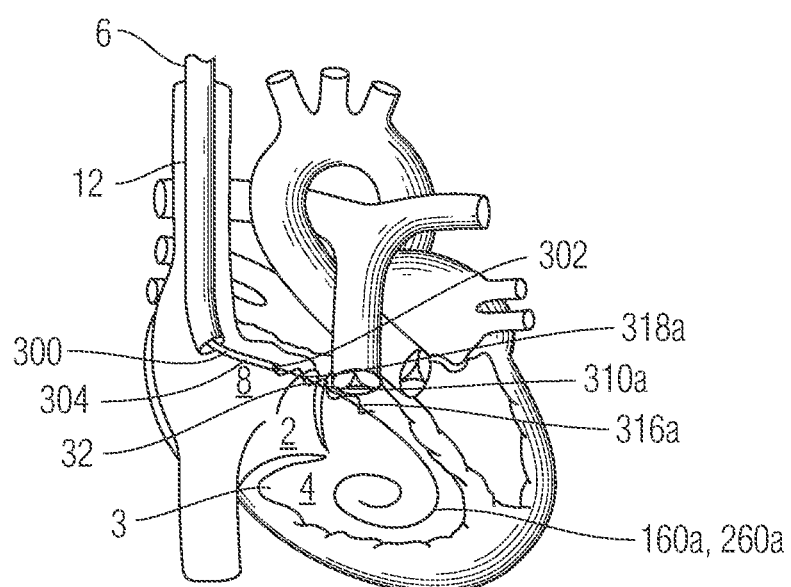
Figure 12C:
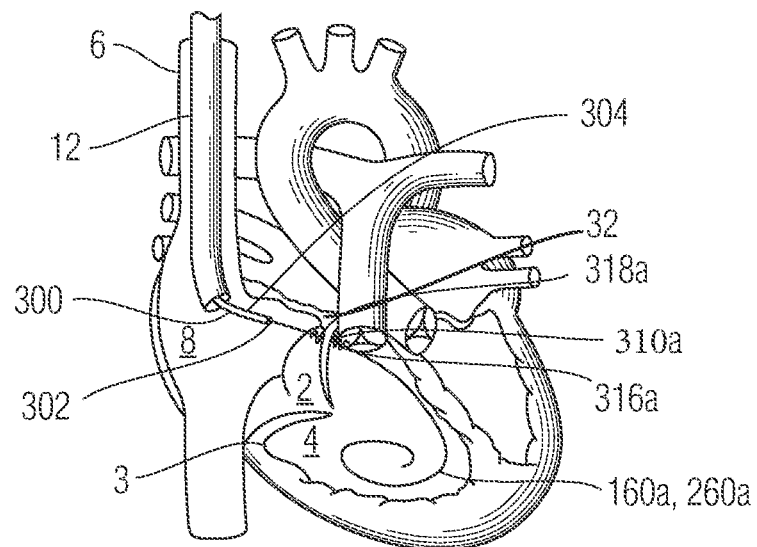

FIGS. 11-12 illustrate an exemplary delivery and deployment of a first tissue anchor (310a) across the tricuspid annulus (3). FIGS. 11a and 12a illustrate the process of exposing of the distal portion (316a) of the tissue anchor (310a) and FIGS. 11b and 12b illustrate the process of exposing the proximal portion (318a) of the tissue anchor (310a), where the tissue anchor tracks along the wire (60a, 160a, 260a) at the location (32) according to the embodiments described in FIGS. 2-9. FIGS. 11c and 12c illustrate an exemplary deployment of the tissue anchor (310a) positioned at the location (32) according to the embodiment described in association with FIGS. 2-9, where the tissue anchor tracks along the wire (60a, 160a, 260a).

Referring to FIGS. 11a and 12a, a tissue anchor delivery catheter (300) holding a tissue anchor (310a) inside its longitudinal lumen (302) tracks along the wire (60a, 160a, 260a), across the tricuspid annulus (3), and into the right ventricle (4). Continuing to refer to FIGS. 11a and 12a, the tissue anchor (310a) is partially pushed distally outside of the distal end (304) of the tissue anchor delivery catheter (300). Once the distal portion (316a) of the tissue anchor (310a) or a sufficient amount of the anchor elements (312, shown in FIG. 10) is exposed inside the right ventricle (4), a clinician stops pushing the tissue anchor (310a) distally and retracts the tissue anchor delivery catheter (300) proximally so that the distal end (304) of the tissue anchor delivery catheter (300) moves proximally across the annulus (3) and back into the right atrium (8). The clinician then exposes the proximal portion (318a) of the tissue anchor (310a) or the remainder of the anchor elements (312) of the tissue anchor (310a) within the right ventricle (4) by further retracting the tissue anchor delivery catheter (300) proximally as shown in FIGS. 11b and 12b.

As illustrated in FIGS. 11c and 12c, to deploy the tissue anchor (310a), the clinician pulls the proximal end of the tensile member (314) such that the anchor elements (312) of the tissue anchor (310a) are drawn together against the opposite sides of the tricuspid annulus (3), thereby securing the first tissue anchor (310a) to the tricuspid annulus (3). As a result, as illustrated in FIGS. 11c and 12c, the first tissue anchor (310a) is deployed across the tricuspid annulus (3) at the first location (32) with the distal portion (316) of the tissue anchor (310a) placed against the atrial side of the tricuspid annulus (3), the proximal portion (318) of the tissue anchor (310a) placed against the ventricle side of the tricuspid annulus (3), and the tensile member (314) of the first tissue anchor (310a) extending proximally through the lumen (302) of the tissue anchor delivery catheter (300) to the outside of the body. According to some embodiments, the wire (60a, 160a, 260a) that marks the first location (32) and maintains the annulus access during the deployment of the first tissue anchor (310a) is then withdrawn proximally outside of the body, while the proximal end of the tensile member (314) is controlled by the clinician from outside of the body.

Although exemplary embodiment herein disclosure proximal and distal portion (316a) of the tissue anchors (310a) are deployed/cinched simultaneously, one skilled in the art should understand that in an alternative embodiment, distal portion (316a) of the tissue anchors (310a) can be deployed/cinched right after being exposed inside the right ventricle (4) and before the tissue anchor delivery catheter (300) being retracted back into the right atrium (8). Upon positioning the deployed/cinched distal portion of the tissue anchor against the right atrium side of the annulus (3), the proximal portion (318a) is then exposed within the right ventricle (4) and further deployed/cinched against the tricuspid annulus (3). One skilled in the art should understand that specific examples disclosed herein should not be viewed as limiting. Similar tissue anchor deployment technique known in the field could also be incorporated herein.

With the first tissue anchor (310a) securely deployed at the first location across the tricuspid annulus (3), the clinician can deploy a second tissue anchor (310b) at a second location (30) according to some embodiments of the present teachings. FIGS. 13-14 illustrate several exemplary deployment of a second tissue anchor (310b) at a second location (30) across the tricuspid annulus (3).

Figure 13A:
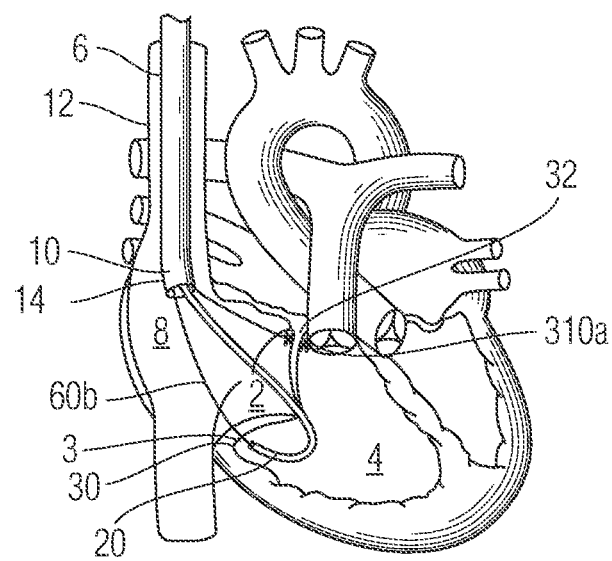
FIGS. 13a-13b are perspective views of an exemplary method where an exemplary second wire extends across the tricuspid annulus in accordance with the present teachings.

According to some embodiments, similar to what is described in FIGS. 2-6, a clinician uses the similar steps to position a wire delivery catheter (20) against the tricuspid annulus (3) from inside the right ventricle (4) at the second location (30). According to some embodiments, the positioning of the wire delivery catheter against the tricuspid annulus includes extending, retracting, turning, or otherwise manipulating the wire delivery catheter (20) to the second location (30) similar to the methods described herein or known to those with ordinary skill in the art. Similar to what is described herein in accordance with the FIGS. 2-6, one end of the second wire (60b) is advanced across the tricuspid annulus (3), captured by the capture basket (44, 52) as illustrated in FIGS. 3a and 3b, and pulled proximally through the lumen (14) of the guide (12) outside of the body. As illustrated in FIG. 13a, it results in that the wire (60) is placed at the second location (30) and both the ends of the wire (60b) are outside of the body.

Figure 13B:
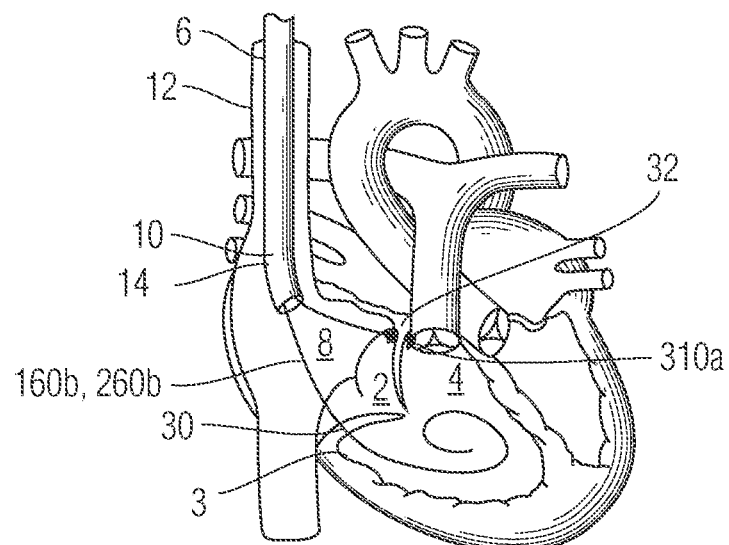

According to alternative embodiments, similar to what is described in FIGS. 7-9, a clinician takes the similar steps to position the wire delivery catheter (120, 220) against the tricuspid annulus (3) from inside the right atrium (8) at a second location (30). According to some embodiments, this is done by extending, retracting, turning, or otherwise manipulating a locating catheter (100) or a locating device (210) at the second location (30) through methods similar to those described herein or known to those with ordinary skill in the art. Similar to what is described in accordance with FIGS. 7-9, the wire delivery catheter (120, 220) is positioned at the second location (30) through magnetic attraction or by the wire delivery catheter design discussed herein. As illustrated in FIG. 13b, a second wire (160b, 260b) is advanced distally across the tricuspid annulus (3) and reaches the right ventricle (4) as described herein. The result is illustrated in FIG. 13b, where one end of the wire (160b, 260b) extends distally through the lumen (14) of the guide (12) and reaches the right ventricle (4). In other words, the distal end of the second wire (160b, 260b) resides inside the right ventricle (4) and the proximal end of the second wire (160b, 260b) resides outside of the body.

Figure 14A:
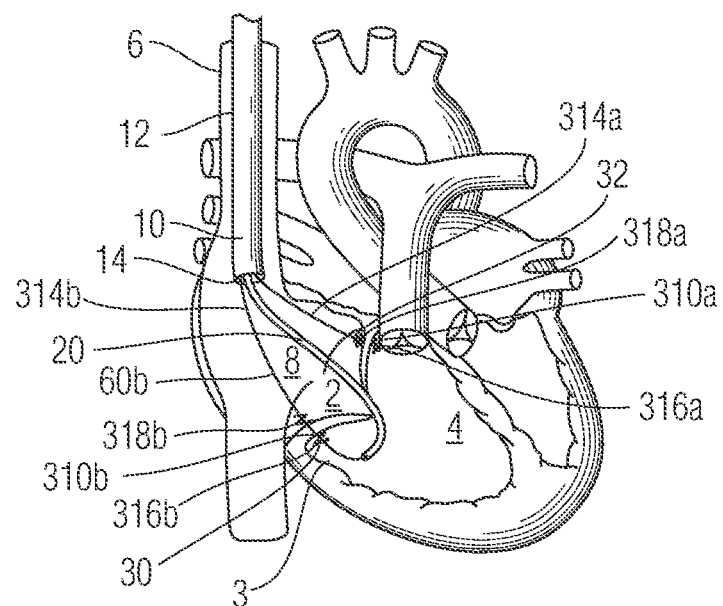
FIGS. 14a-14b are perspective views of an exemplary second tissue anchor deployed across the tricuspid annulus in accordance with the present teachings.
Figure 14B:
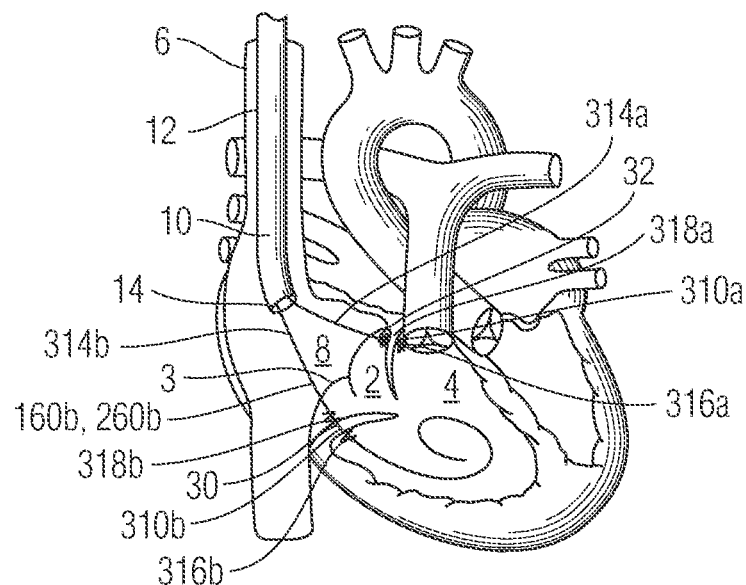

In various embodiments, a second tissue anchor (310b) is deployed at the second location (30) according to various embodiments described herein in accordance with FIGS. 11-12. FIGS. 14a and 14b illustrate the embodiments where the second tissue anchor (310b) is deployed across the tricuspid annulus (3) at the second location (30) with the distal portion (316b) of the second tissue anchor (310b) placed against the ventricle side of the annulus (3), the proximal portion (318b) of the tissue anchor (310b) placed against the atrial side of the annulus (3), and the tensile member (314) of the second tissue anchor (310b) extending proximally through the venous access to the outside of the body. At this point, the second wire (60b, 160b, 260b) can be removed.

Figure 15:
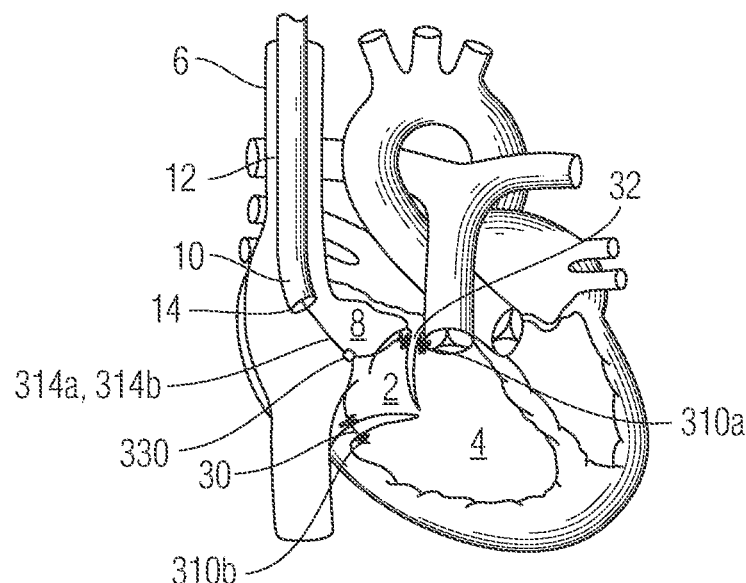
FIG. 15 is a perspective view of applying tension to two exemplary tissue anchors deployed across annulus in accordance with the present teachings.

FIG. 15 illustrates an exemplary bicuspidization of a tricuspid valve (2). According to some embodiments, a clinician applies tension to one or both of the tensile members (314a, 314b) of the tissue anchors (310a, 310b). This tension pulls two tissue anchors (310a) closer to each other, thereby reducing the circumference of the tricuspid annulus (3). This tension, and the reduced distance between the two tissue anchors (310a, b), are maintained by directing a locker member (330) along the tensile members (314a, 314b) towards the tissue anchors (310a, 310b). Suitable lockers include those well known in the art and those described in U.S. application Ser. No. 11/753,921, filed on May 25, 2007, entitled Lockers for Surgical Tensile Members and Methods of Using the Same to Secure Surgical Tensile Members, the disclosure of which is incorporated herein by reference. With the tensile members (314a, 314b) are secured by the locker (330), the excess tensile members (314a, 314b) proximal to the locker (330) can be removed by a cutter, for example, a cutter disclosed in U.S. patent application Ser. No. 11/935,054, filed on Nov. 5, 2007, entitled Suture Cutter and Method of Cutting Suture, the disclosure of which is incorporated herein by reference. The guide (12) along with all the wire delivery catheters (20, 120, 220) and/or the tissue anchor delivery catheter (300) can then be retracted proximally and removed.

FIGS. 16a and 16b illustrate an exemplary process of bicuspidization. According to some embodiments, the first tissue anchor (310a) is deployed at a location at or close to the commissure of the posterior and septal leaflets and the second tissue anchor (310b) is deployed at a location at or close to the commissure of the posterior and anterior leaflets, as illustrated in FIG. 16a. Upon reducing the distance between the two tissue anchors (310a, 310b), the posterior annulus is shortened and the posterior leaflet is effectively eliminated, thereby turning the three-leaflet valve into a two-leaflet valve. In certain instances, the process is called bicuspidization, as illustrated in FIG. 16b.

According to various embodiments of the present teachings, reducing the circumference of the tricuspid annulus (3) facilitates a coaptation of the tricuspid valve (2) leaflets and reduces or eliminates the tricuspid regurgitation jet by at least one degree. According to some embodiments, both the tissue anchors (310a, 310b) are positioned along the posterior annulus. According to other embodiments, at least one tissue anchor (310a) is positioned on the posterior annulus and the other tissue anchor (310b) is placed on the anterior annulus or the septal annulus. According to yet other embodiments, at least one tissue anchor (310a) is placed at a location at or close to the commissure of the posterior and septal leaflets and the other tissue anchor (310b) is placed at a location between the commissure of the posterior and septal leaflets and the commissure of the posterior and anterior leaflets.

According to some embodiments, two tissue anchors (310a and 310b) are deployed around the annulus circumferences. According to other embodiments, more than two tissue anchors (310a, 310b) are deployed. One exemplary embodiment as shown in FIGS. 16c and 16d, includes one tissue anchor (310a) deployed at an location at or close to the commissure of the posterior and septal leaflets, one tissue anchor (310b) deployed at an location at or close to the commissure of the posterior and anterior leaflets, and another tissue anchor (310c) deployed approximately in the middle of the first two. One with ordinary skill in the art would understand that although FIGS. 16a-16d illustrate certain embodiments of the present teachings, other configuration and other locations can also be used for placing the tissue anchor (310a). For example, four or more tissue anchors could be implanted along the posterior annulus of the tricuspid valve. Thus, what is described as to the locations of the tissue anchor (310a) or the number of the tissue anchors (310a) deployed should not be viewed as limiting.

Figure 16E:
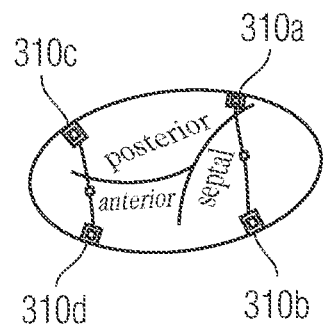
Figure 16F:
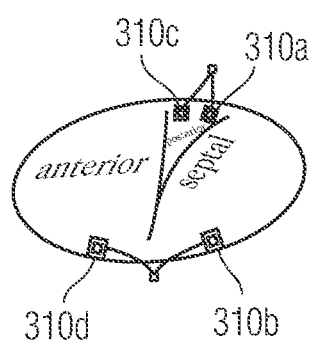

Additionally, although three tissue anchors are illustrated herein, more than three tissue anchors can also be used without departing from the scope of the present teachings. According to some embodiments, tension is applied to all tissue anchors and secured by one locker. According to other embodiments, tension is applied to two of the tissue anchors at a time, for example, as illustrated in FIGS. 16e and 16f.

According to some embodiments, each tissue anchor is deployed sequentially. Specifically, the embodiments described in accordance with FIGS. 2-15 allow a clinician to place a wire (60, 160, 260) at the first location (32), followed by deploying a first tissue anchor (310a) over the wire (60, 160, 260), and then manipulate the same wire delivery mechanism to and place the wire at a second location (30), followed by deploying a second tissue anchor (310b) over the wire (60, 160, 260). According other embodiments, two or more tissue anchors are deployed simultaneously. Specifically, a multi-lumen translation catheter (400) can be used to place two wires at two locations at the same time. According to other embodiments, a catheter with more than two branches can be used to place multiple wires at multiple locations at the same time.

Figure 17:
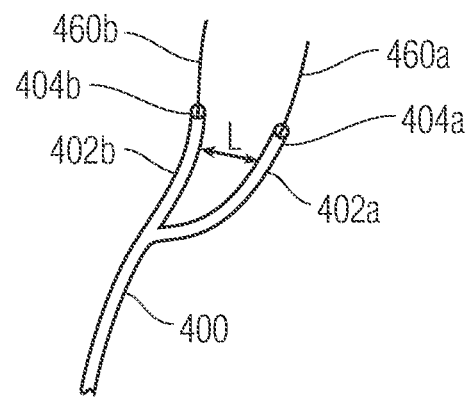
FIG. 17 is a perspective view of an exemplary multi-lumen translation catheter in accordance with the present teachings.

FIGS. 17-19 illustrate the use of a multi-lumen translation catheter (400) to place two wires (460a, 460b) across the tricuspid annulus (3). According to one embodiment, as illustrated in FIG. 17, a multi-lumen translation catheter (400) comprises a first catheter member (402a) having a first lumen (404a) for a first wire (460a) and a second catheter member (402b) having a second lumen (404b) for a second wire (460b). The first and second wires (460a, 460b) are slidably disposed within the first and second catheter lumens (404a, 404b), respectively. There is a pre-defined lateral distance "L" between the first catheter member (402a) and the second catheter member (402b).

Figure 18A:
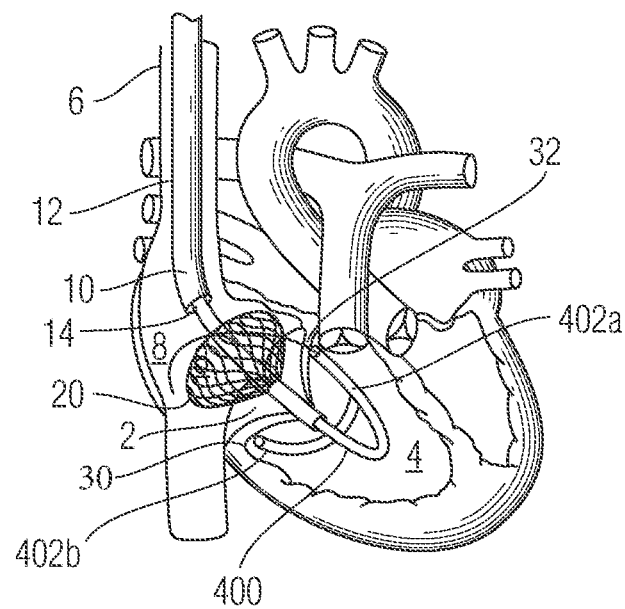
FIGS. 18a-18b are perspective views of an example of placing two exemplary wires across the tricuspid annulus with an exemplary multi-lumen translation catheter in accordance with the present teachings.

According to some embodiments, a multi-lumen translation catheter (400) is delivered to the right ventricle (4) and positioned against the tricuspid annulus (3) through a wire delivery catheter (20), as illustrated in FIG. 2a. According to some embodiments, similar to what is described herein in accordance with FIGS. 2-6, upon the wire delivery catheter (20) being positioned against the tricuspid annulus (3) from inside the right ventricle (4), the first wire (460a), extending through the lumen (404a) of the first catheter member (402a), is placed across the tricuspid annulus (3). The wire delivery catheter (20) is retracted proximally, exposing the second catheter member (402b) of the multi-lumen translation catheter (400), as illustrated in FIG. 18a. Once outside of the distal end (24) of the wire delivery catheter (20), the second catheter member (402b) expands laterally away from the first catheter member (402a) to a pre-defined distance. Without losing the placement of the first wire (460a), a clinician can turn the multi-lumen translation catheter (400) and/or the wire delivery catheter (20) so that the second catheter member (402b) is positioned at a second location (30). A second wire (460b) is then advanced across the tricuspid annulus (3) following the steps described herein and shown in FIGS. 4a and 4b.

According to some embodiments, both the wires (460a, 460b) is captured by the capture device and the distal ends of the both wires (460a, 460b) are then withdrawn through the lumen (14) of the guide (12) outside of the body. As a result, as illustrated in FIG. 18b, two wires are placed at two locations, which can be used to facilitate the deployment of two tissue anchors (310a), following the steps discussed above and in accordance with FIGS. 11a-11c.

Figure 19A:
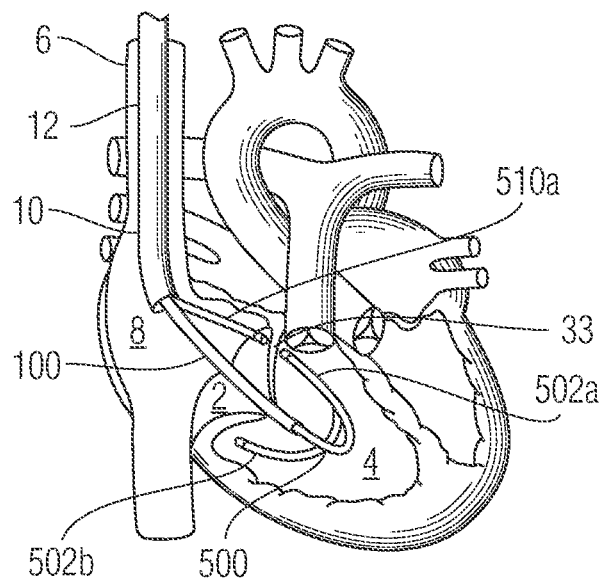
FIGS. 19a-19b are perspective views of an example of placing two exemplary wires across the tricuspid annulus with an exemplary multi-lumen translation catheter in accordance with the present teachings.

According to other embodiments as illustrated in FIG. 19a, a multi-lumen translation catheter or device (500) is delivered though the lumen of a locating catheter (100) to the right ventricle (4). As the distal end (104) of the locating catheter (100) is positioned against the annulus (3), a first catheter member (502a) is placed at a first location (32), attracting a first wire delivery catheter (510a) and facilitating the placement of a first wire (560a). The locating catheter (100) is retracted proximally, exposing a second catheter member (502b) of the multi-lumen translation catheter (500) as illustrated in FIG. 19a. Once outside of the distal end (104) of the locating catheter (100), the second catheter member (502b) expands laterally away from the first catheter member (502a) to a pre-defined distance. Without losing the placement of the first wire delivery catheter (510a), a clinician can turn the multi-lumen translation catheter (500) and/or the locating catheter (100) so that the second catheter member (502b) is positioned at a second location (30). The second catheter member (502b) attracts the second wire delivery catheter (510b) and facilitates the placement of the second wire (560b) across the tricuspid annulus (3) as shown in FIG. 19b.

According to some embodiments, the multi-lumen translation catheter is placed at two locations first and two wires are placed across the tricuspid annulus simultaneously or sequentially. Alternatively, in other embodiments, a first catheter member of a multi-lumen translation catheter is positioned at a first location first and a first wire is placed across the tricuspid annulus; a second catheter member of the multi-lumen translation catheter is positioned at a second location and a second wire is placed across the tricuspid annulus.

Figure 18B:
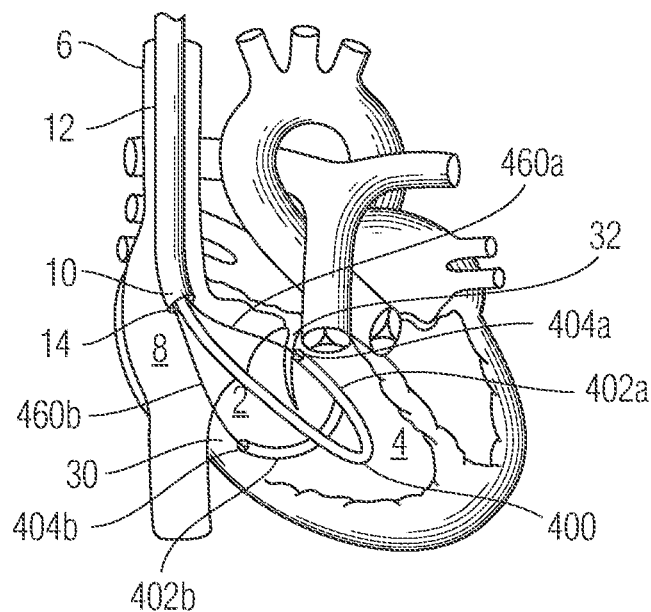
Figure 19B:
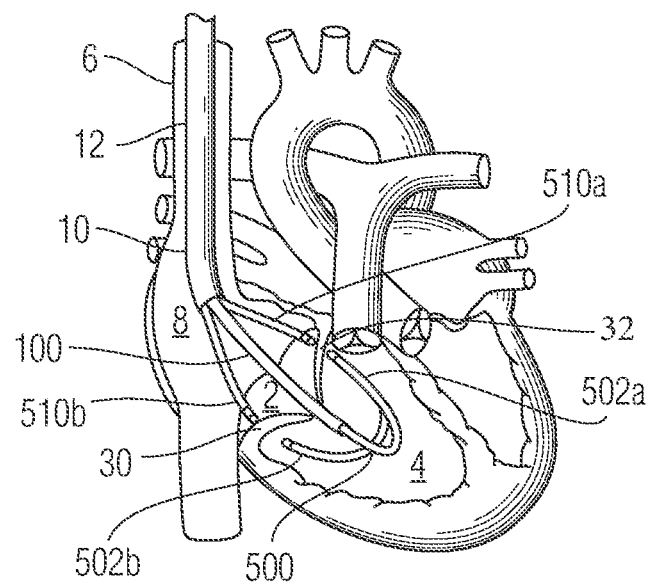

As a result, as illustrated in FIGS. 18b and 19b, two wires are placed at two locations, followed by the deployment of two tissue anchors according to the steps or steps similar with those discussed herein and in accordance with FIGS. 11-16.

Although an exemplary multi-lumen translation catheter is described above, one with ordinary skill in the art would understand that a three or more branched catheter can be used without departing from the spirit of the present teachings. The multi-lumen translation described in conjunction with the drawings of the present teachings have some similarities to those in U.S. patent application Ser. No. 11/685,239, filed on Mar. 13, 2007, entitled Systems and Methods for Introducing Elements Into Tissue; U.S. patent application Ser. No. 11/685,240, filed on Mar. 13, 2007, entitled Tissue Anchors, Systems, and Methods, and Devices; U.S. patent application Ser. No. 11/685,242, filed on Mar. 13, 2007, entitled Devices and Methods For Introducing Elements into Tissue; and U.S. patent application Ser. No. 13/282,139, filed on Oct. 26, 2011, entitled Hand Operated Device for Controlled Deployment of a Tissue Anchor and Method of Using the Same; each of which is incorporated in its entirety by reference herein.

Above described embodiment discloses the use of one locker member maintaining tension on two or more tensile members. In alternative embodiments of the present teaching, tricuspid annulus can be plicated by a chain of tissue anchors. In some embodiments, two or more tissue anchors are connected together by a tensile member. Plication happens by pulling said tensile member and thereby drawing all tissue anchors together.

Figure 20A:
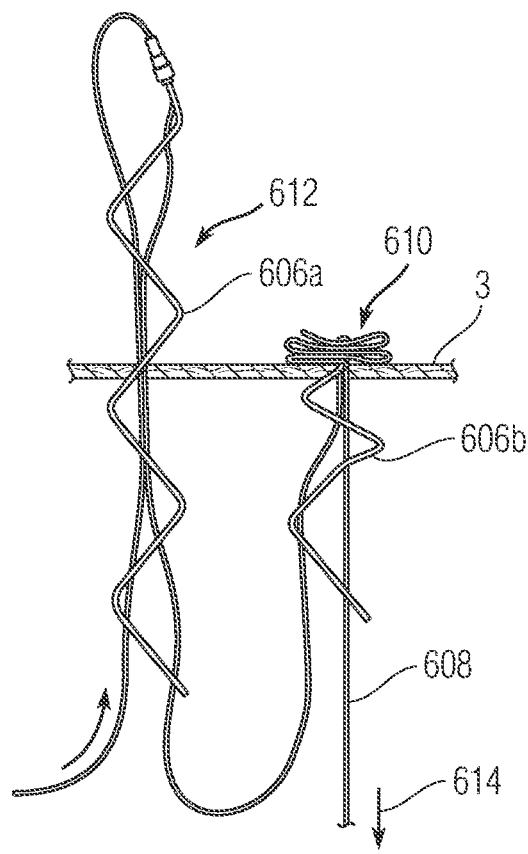
FIGS. 20a-20c are perspective views of placing multiple tissue anchors across the tricuspid annulus in accordance with the present teachings.
Figure 20B:
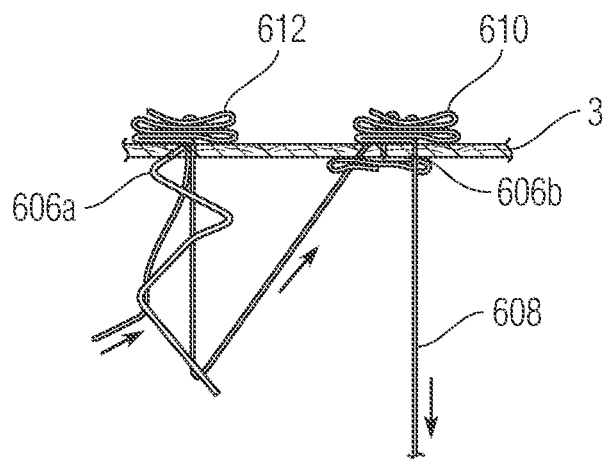
Figure 20C:
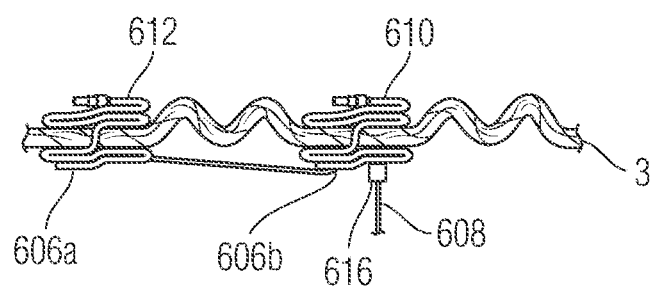

FIGS. 20A-C illustrates one embodiment of the present teaching where a single tensile member may be used to deploy, fasten and draw together at least two separate tissue anchors. As shown in FIG. 20A, first and second tissue anchors (610, 612) are deployed at spaced apart locations along the tricuspid valve annulus (3). Each tissue anchors (610, 612) includes an elongate strip (606a, 606b) of flexible material, such as fabric or other material as described above, as well as a single tensile member (608) extending through each of the elongate strips (606a, 606b). Upon deployment of the two tissue anchors (610, 612), the free end (614) of the tensile member (608) is pulled thereby securely fastening the first tissue anchor (610) as shown in FIG. 20A and subsequently securely fastening the second tissue anchor (612) to the annulus (3) tissue as shown in FIG. 20B. Upon further tensioning of the tensile member (608), the tissue anchors (610, 612) will be drawn together to plicate the tissue therebetween as shown in FIG. 20C. A locker member (616) may then be used to lock in the desired amount of plication by lock the free end (614) of the tensile member (608) as shown in FIG. 20C. The free end (614) of the tensile member (608) may then be cut to appropriate length. One skilled in the art should understand that more than two tissue anchors could be used with this teaching.

Figure 21A:
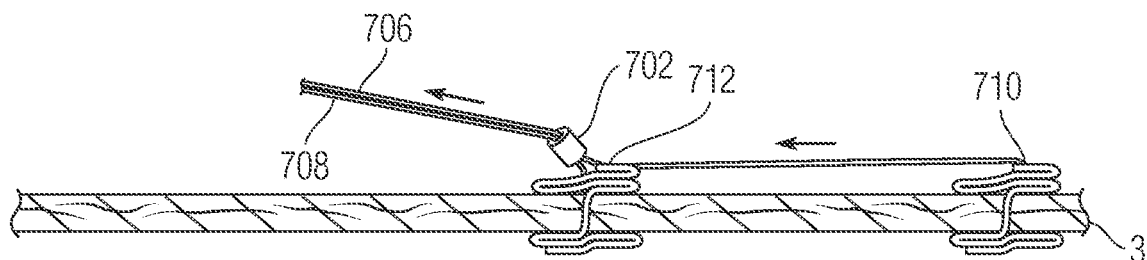
FIGS. 21a-21c are perspective views of placing multiple tissue anchors across the tricuspid annulus in accordance with the present teachings.
Figure 21B:
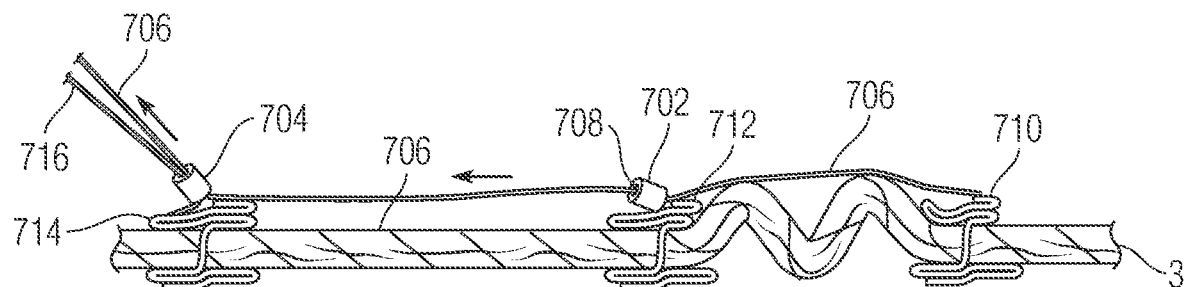
Figure 21C:
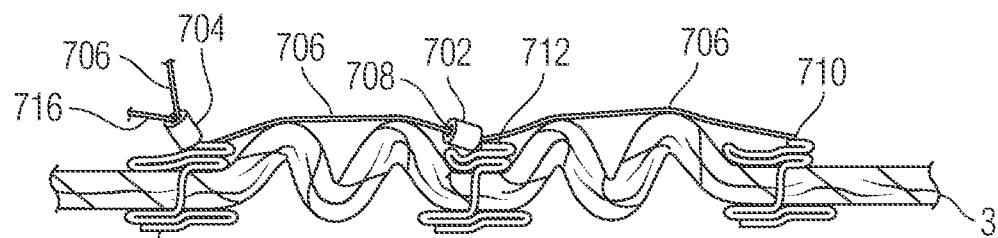

FIGS. 21A-21C illustrates another embodiment of the present teaching where tricuspid annulus is plicated by a chain of tissue anchors. Similar to above described methods, two tissue anchors (710,712) are secured to tricuspid annulus (3), each with a tensile member (706, 708) extending proximally. FIG. 21A illustrates that the tensile members (706, 708) extend through a first locker member (702). Suitable locker members can include those described in U.S. patent application Ser. No. 11/425,731 and U.S. patent application Ser. No. 11/753,921, the disclosures of which are incorporated herein by reference, or other suitable lockers known within the art. The first locker member (702) can include a locker body having a passageway through which the tensile members (706, 708) extend. A slidable member can be positioned within the passageway, which can be moved from a latent condition to an activated condition to prevent the tensile members (706, 708) from moving relative to the locker body. Both tensile members (706, 708) are pulled proximally by the clinician. Upon plicating annulus tissue between the first tissue anchor (710) and the second tissue anchor 712, the tensile members (706, 708) are locked by the first locker member (702) to preserve the plications created by tensioning as illustrated in FIG. 21B. According to some embodiments of the present teaching, a suture cutter is then advanced along tensile members (706, 708) to just proximal to the first locker member (702). In one embodiment, tensile member (708) from the second tissue anchor (712) is cut while the tensile member (706) from the first tissue anchor (710) remains intact. In another embodiment, tensile member (706) from the second tissue anchor (710) is cut while the tensile member (708) from the first tissue anchor (712) remains intact.

According to some embodiments, to create a chain of plications, a clinician can then repeat method of tissue plication described above and extend the first tensile member (706) from the first tissue anchor (710) to a second locker member (704). As illustrated in FIG. 21B, a third tissue anchor (714) is further deployed across the posterior annulus (3) with a third tensile member (716) extending proximally. Upon plicating annulus tissue between the first tissue anchor (710), and the third tissue anchor (714), the tensile members (706, 716) are locked by the second locker member (704) to preserve the plication created by tensioning as illustrated in FIG. 21C. The second locker member (704) can be the same as the first locker member (702), or if desired, a different suitable locker can be used. When tension is applied to the tensile members (706, 716), the tissue of the posterior annulus (3) is further plicated. This plication further reduces the size of the tricuspid valve orifice.

According to some embodiment, a suture cutter can then be advanced to cut the tensile members (706, 716) just proximal to the second locker member (704). However, if plication is not complete such that the posterior, anterior and septal leaflets do not coapt, then additional tissue anchors can be advanced to the annular tissue. Accordingly, at least one of the tensile members (706, 716) remains intact to be tensioned with a subsequently positioned tissue anchor.

According to various embodiments of the present teachings, a radiopaque marker or textured surface can be used to make the device visible by using radiographic imaging equipment such as an X-ray, magnetic resonance, ultrasound or other imaging technique. A marker disclosed herein may be applied to any part of the guide, catheter, or devices disclosed in present teachings. A radiopaque marker can be sewed, adhered, swaged riveted, or otherwise placed and secured on the guide, catheter, and/or devices. The radiopaque marker may be made from a material selected from tantalum, tungsten, platinum, iridium, gold, an alloy thereof, or another material known to those with ordinary skill in the art. The radiopaque marker can also be made from cobalt, fluorione, or another paramagnetic material, or another MR visible material known to those with ordinary skill in the arts. Additionally, a contrast media injected into the atrium, ventricle, or artery may also be used to confirm the positioning under a fluoroscope.

Unless otherwise defined, all technical and scientific terms used herein have the same meaning as commonly understood by one of ordinary skill in the art to which this present teachings belong. Methods and materials similar or equivalent to those described herein can be used in the practice or testing of the present teachings. In case of conflict, the specification, including definitions, controls. In addition, the materials, methods, and examples are illustrative only and not intended to be limiting.

The invention claimed is:
1. A method, comprising:
transluminally advancing a first end of a wire toward a first cardiovascular site via a vena cava of a subject;
transluminally penetrating the first end of the wire through tissue at the first cardiovascular site;
transluminally advancing a capture device into the subject;
using the capture device, capturing the first end of the wire and pulling the first end of the wire away from the first cardiovascular site;

from the first end of the wire, tracking a first anchor along the wire, and subsequently anchoring the first anchor to the tissue at the first cardiovascular site;

anchoring a second anchor to tissue at a second cardiovascular site of the subject; and subsequently, drawing together the first cardiovascular site and the second cardiovascular site by applying tension between the first anchor and the second anchor.

2. The method according to claim 1, further comprising tracking the second anchor along the wire prior to anchoring the second anchor.

3. The method according to claim 1, further comprising transluminally advancing a locker, and using the locker to maintain the tension between the first anchor and the second anchor.

4. The method according to claim 1, wherein penetrating the first end of the wire through the tissue at the first cardiovascular site comprises piercing the tissue at the first cardiovascular site with the first end of the wire.

5. The method according to claim 1, wherein penetrating the first end of the wire through the tissue at the first cardiovascular site comprises making a hole in the tissue at the first cardiovascular site using radio frequency energy.

6. The method according to claim 1, wherein:
the method further includes transluminally advancing the first end of the wire to the first cardiovascular site while the first end of the wire is disposed within a catheter, and penetrating the first end of the wire through the tissue at the first cardiovascular site comprises piercing a hole in the tissue at the first cardiovascular site with an extendable needle of the catheter, and advancing the first end of the wire out of the catheter and through the hole.

7. The method according to claim 1, wherein transluminally penetrating the first end of the wire through the tissue at the first cardiovascular site comprises transluminally penetrating the first end of the wire through the tissue at the first cardiovascular site while a second end of the wire remains disposed outside of the subject.

8. The method according to claim 7, wherein pulling the first end of the wire away from the first cardiovascular site comprises pulling the first end of the wire away from the first cardiovascular site while the second end of the wire remains disposed outside of the subject.

9. The method according to claim 1, wherein the tissue is tissue of a heart of the subject, and penetrating the first end of the wire through the tissue at the first cardiovascular site comprises penetrating the first end of the wire through the tissue of the heart.

10. The method according to claim 9, wherein the tissue is tissue of a valve of the heart, and penetrating the first end of the wire through the tissue of the heart comprises penetrating the first end of the wire through the tissue of the valve.

11. The method according to claim 10, wherein the valve is a tricuspid valve of the heart, and penetrating the first end of the wire through the tissue of the valve comprises penetrating the first end of the wire through tissue of the tricuspid valve.

12. The method according to claim 11, wherein drawing together the first cardiovascular site and the second cardiovascular site comprises drawing together the first cardiovascular site and the second cardiovascular site in a manner that reshapes the tricuspid valve.

13. The method according to claim 12, wherein the first cardiovascular site is near a commissure of an anterior leaflet of the tricuspid valve and a posterior leaflet of the tricuspid valve, and wherein penetrating the first end of the wire through the tissue at the first cardiovascular site comprises penetrating the first end of the wire through tissue near the commissure of the anterior leaflet and the posterior leaflet.

14. A method, comprising:
transluminally penetrating a first end of a wire through a tricuspid valve at a first cardiovascular site of a subject;

transluminally advancing a capture device into the subject;

using the capture device, capturing the first end of the wire and pulling the first end of the wire away from the first cardiovascular site;

from the first end of the wire, tracking a first anchor along the wire, and subsequently anchoring the first anchor to the tissue at the first cardiovascular site;

anchoring a second anchor to tissue at a second cardiovascular site of the subject; and subsequently, drawing together the first cardiovascular site and the second cardiovascular site by applying tension between the first anchor and the second anchor.

15. A method, comprising:
positioning a first end of a wire at a first cardiovascular site of a subject facilitated by a radiopaque member positioned within a blood vessel adjacent to the first cardiovascular site;

transluminally penetrating the first end of the wire through tissue at the first cardiovascular site;

transluminally advancing a capture device into the subject;

using the capture device, capturing the first end of the wire and pulling the first end of the wire away from the first cardiovascular site;

from the first end of the wire, tracking a first anchor along the wire, and subsequently anchoring the first anchor to the tissue at the first cardiovascular site;

anchoring a second anchor to tissue at a second cardiovascular site of the subject; and subsequently, drawing together the first cardiovascular site and the second cardiovascular site by applying tension between the first anchor and the second anchor.

* * * * *